United States Patent
Wheeler

(10) Patent No.: US 8,415,317 B2
(45) Date of Patent: *Apr. 9, 2013

(54) ADJUVANT COMPOSITIONS AND METHODS FOR ENHANCING IMMUNE RESPONSES TO POLYNUCLEOTIDE-BASED VACCINES

(75) Inventor: Carl J. Wheeler, Poway, CA (US)

(73) Assignee: Vical Incorporated, San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 13/031,064

(22) Filed: Feb. 18, 2011

(65) Prior Publication Data

US 2011/0165197 A1    Jul. 7, 2011

Related U.S. Application Data

(60) Division of application No. 11/889,980, filed on Aug. 17, 2007, now abandoned, which is a continuation of application No. 10/391,216, filed on Mar. 19, 2003, now Pat. No. 7,582,613, which is a division of application No. 09/534,943, filed on Mar.

(Continued)

(51) Int. Cl.
| A61K 48/00 | (2006.01) |
| A61K 51/00 | (2006.01) |
| A61K 39/00 | (2006.01) |
| A61K 39/012 | (2006.01) |
| A61K 45/00 | (2006.01) |
| C12N 15/00 | (2006.01) |
| C07H 21/02 | (2006.01) |
| A61P 33/00 | (2006.01) |

(52) U.S. Cl. .......... 514/44 R; 435/320.1; 435/455; 424/1.11; 424/184.1; 424/265.1; 424/278.1; 536/23.1; 514/4.6

(58) Field of Classification Search .......... None
See application file for complete search history.

(56) References Cited

U.S. PATENT DOCUMENTS

| 5,264,618 A | 11/1993 | Felgner et al. |
| 5,334,761 A | 8/1994 | Gebeyehu et al. |
| 5,459,127 A | 10/1995 | Felgner et al. |
| 5,580,859 A | 12/1996 | Felgner et al. |
| 5,589,466 A | 12/1996 | Felgner et al. |
| 5,641,665 A | 6/1997 | Hobart et al. |
| 5,676,954 A | 10/1997 | Brigham et al. |
| 5,693,622 A | 12/1997 | Wolff et al. |

(Continued)

FOREIGN PATENT DOCUMENTS

| WO | WO 94/29469 A2 | 12/1994 |
| WO | WO 97/19675 A2 | 6/1997 |

(Continued)

OTHER PUBLICATIONS

Scott-Taylor et al., 2000 Exp. Opin. Invest. Drugs 9:471-480.*

(Continued)

*Primary Examiner* — Robert M Kelly
*Assistant Examiner* — Kelaginamane T Hiriyanna
(74) *Attorney, Agent, or Firm* — Sughrue Mion, PLLC

(57) ABSTRACT

The invention provides adjuvants, immunogenic compositions, and methods useful for polynucleotide-based vaccination and immune response. In particular, the invention provides an adjuvant of cytofectin:co-lipid mixture wherein cytofectin is GAP-DMORIE.

17 Claims, 13 Drawing Sheets

| Plasmid | Leader | Gene | Promoter | Enhancer | Intron | Terminator |
|---------|--------|------|----------|----------|--------|------------|
| VR4700 | tissue plasminigen activator | influenza A/PR/8/34 nucleoprotein | CMV | CMV | CMV-A | mRBG |
| VR5900 | hen egg lysozyme | hen egg lysozyme | CMV | CMV | CMV-A | mRBG |
| VR1412 | not secreted | E. coli Lac Z | CMV | CMV | CMV-A | BGH |
| VR1623 | mouse immunoglobulin | mouse Id/humanFc | CMV | CMV | CMV-A | BGH |
| VR1904 | human factor IX | human factor IX | CMV | CMV | CMV-A | BGH |

Related U.S. Application Data 24, 2001, now Pat. No. 6,586,409, and a continuation of application No. 09/937,604, filed as application No. PCT/US00/08282 on Mar. 24, 2000, now Pat. No. 7,105,574, said application No. 09/937,604 is a continuation of application No. 09/534,943, filed on Mar. 24, 2000, now Pat. No. 6,586,409.

(60) Provisional application No. 60/126,340, filed on Mar. 26, 1999.

(56) References Cited

U.S. PATENT DOCUMENTS

| | | |
|---|---|---|
| 5,703,055 A | 12/1997 | Felgner et al. |
| 5,705,385 A | 1/1998 | Bally et al. |
| 5,861,397 A | 1/1999 | Wheeler |
| 5,866,553 A | 2/1999 | Donnelly et al. |
| 5,910,488 A | 6/1999 | Nabel et al. |
| 5,976,567 A | 11/1999 | Wheeler |
| 5,994,317 A | 11/1999 | Wheeler |
| 6,022,874 A | 2/2000 | Wheeler |
| 6,147,055 A | 11/2000 | Hobart et al. |
| 6,228,844 B1 | 5/2001 | Wolff et al. |
| 6,235,310 B1 | 5/2001 | Wang et al. |
| 6,399,588 B1 | 6/2002 | Hobart et al. |
| 6,586,409 B1 | 7/2003 | Wheeler |
| 6,670,332 B1 | 12/2003 | Wheeler |
| 6,696,424 B1 | 2/2004 | Wheeler |
| 6,706,694 B1 | 3/2004 | Wolff et al. |
| 6,867,195 B1 | 3/2005 | Felgner et al. |
| 6,875,748 B2 | 4/2005 | Manthorpe et al. |
| 7,105,574 B1 | 9/2006 | Wheeler |
| 7,250,404 B2 | 7/2007 | Felgner et al. |
| 7,268,120 B1 | 9/2007 | Horton et al. |
| 7,582,613 B2 | 9/2009 | Wheeler |
| 2003/0915441 | 5/2003 | Parker et al. |
| 2003/0186913 A1 | 10/2003 | Wolff et al. |
| 2003/0191082 A1 | 10/2003 | Wheeler |
| 2003/0203863 A1 | 10/2003 | Hobart et al. |
| 2004/0157789 A1 | 8/2004 | Geall et al. |
| 2004/0162256 A1 | 8/2004 | Geall et al. |
| 2004/0171572 A1 | 9/2004 | Wheeler |
| 2004/0209241 A1 | 10/2004 | Hermanson et al. |
| 2005/0064107 A1 | 3/2005 | Komori et al. |
| 2007/0105193 A1 | 5/2007 | Vilalta et al. |
| 2007/0105799 A1 | 5/2007 | Hermanson |

FOREIGN PATENT DOCUMENTS

| | | |
|---|---|---|
| WO | WO 00/57917 A2 | 10/2000 |

OTHER PUBLICATIONS

Gregoriadis, G., et al., "Liposome-mediated DNA vaccination," FEBS lett. 402:107-110, Elsevier Science B.V. (1997).

Heppell, J., et al., "Development of DNA vaccines for fish: vector design, intramuscular injection and antigen expression using viral haemorrhagic septicaemis virus genes as model," Fish & Shellfish Immunology 8:271-286, Academic press Limited (1998).

Ishii, N. et al., "Cationic lipsomes are a strong adjuvant for a DNA vaccine of human immunodeficiency virus type 1," AIDS res. Hum. Retroviruses 13:1421-1428, Mary Ann Lieber, Inc. (1997).

Klavinskis, L. S. et al., "Mucosal immunization with DNA-liposome complexes," Vaccine 15:818-820, Elsevier science Ltd. (1997).

Kofta, W. et al., "c-DNA vaccination against parasitic infections: advantages and disadvantages," Veterinary parasitology 100:3-12 p. 4-5, Elsevier Science Ltd. (2001).

Locher, C. P., et al., "Human immunodeficiency virus type 2 DNA vaccine provides partial protection from acute baboon infection," Vaccines 22:2261-2272, Elsevier Ltd (Jun. 2004).

Abbas, A. K. et al., "Functional diversity of helper T lymphocytes,"Nature 383:787-793, MacMillan Journals Ltd. (1996).

Lodmell, D. L., et al.,"DNA immunization protects nonhuman primates against rabies virus," Nature Medicine 4:949-952, Nature Publishing Company (1998).

Margalith, M., et al., "Sustained protective rabies neutralizing antibody titers after administration of cationic lipid-formulated pDNA vaccine," Genet. Vaccines Ther. 4:2-7, BioMed Central (Feb. 2006).

Sankar, V. et al., "Salivary gland delivery of pDNA-cationic lipoplexes elicits systemic immune responses," Oral Dis. 8:275-281, Blackwell Munksgaard (Nov. 2002).

Scott-Taylor, T. H. et al. "DNA vaccines," Exp. Opin. Invest. Drugs 9:471-480, Informa Healthcare (2000).

Stephan, D. J. et al., "A New Cationic Liposome DNA Complex Enhances the Efficiency of Arterial Gene Transfer in Vivo," Hum. Gene Ther. 7:1803-1812, Mary Ann Liebert, Inc. (1996).

Ulmer, J.B., et al., "DNA vaccines," Current Opinion in Immunology 8:531-536, Current Biology (1996).

Ulmer, J.B. et al. , "Heterologous Protection Against Influenza by Injection of DNA Encoding a Viral Protein," Science 259:1745-1749, American Association for the Advancement of Science (1993).

Vanderzanden, L., et al., "DNA Vaccines Expressing either the GP or NP Genes of Ebola Virus Protect Mice from Lethal Challenge," Virology 246:134-144, Academic Press (1998).

Vical Incorporated, "Single Injection of Vical's Avian Flu DNA Vaccine Provides 100% Protection in Ferrets," Vical Oct. 10, 2006 News Release, Vical Incorporated (2006).

Norman, J. A. et al., "Development of improved vectors for DNA-based immunization and other gene therapy applications," Vaccine 15:801-803, Elsevier Science Ltd (1997).

Norman, J. et al., "Adjuvant for plasmid DNA Vaccines" in Methods in Molecular Medicine, vol. 29, DNA Vaccines: Methods and Protocol, Lowrie D. B. and R.G. Whalen, eds. Humana Press Inc., Totowa NJ, oo.185-196 (Aug. 1999).

Nukuzuma, C., et al., "Enhancing effect of vaxfectin on the ability of a Japanese Encephalitis DNA vaccines to induce neutralizing antibody in mice," Viral immunology 16:183-189, Mary Ann Liebert, Inc. (2003).

Okada, E. et al.,"Intranasal Immunization of a DNA vaccines with IL-12-and Granulocyte macrophage colony-stimulating factor (GM-CSF)-expressing plasmids in liposome induced strong mucosal and cell-mediated immune responses against HIV-1 Antigens," J. Immunol. 159:3638-3647, American Association of Immunologists (1997).

Parker , S. et al. , "Tissue Distribution of the Cytofectin Component of a Plasmid-DNA/Cationic Lipid Complex Following Intravenous Administration in Mice," Hum. Gene Ther. 8:393-401, Mary Ann Liebert, Inc. (1997).

Rajcani, J., et al., "Current developments in viral DNA vaccines: shall they solve the unsolved?," Rev. Med. Virol. 15:303-325, Wiley (2005).

Raz, E. et al., "Preferential induction of a Th1 immune response and inhibition of specific IgE antibody foration by plasmid DNA immunization," Proc. Natl. Acad. Sci. USA 93:5141-5145, The National Academy of Sciences of the United States of America (1996).

Agadjanyan, M.G., et al.,"DNA plasmid based vaccination against the oncogenic human T cell leukemia virus type 1," Current Topics in Microbiology and Immunology 226:175-192, Springer Verlag (1998).

Barnfield, C. et al.,"The cellular basis of immune induction at mucosal surfaces by DNA vaccination" Developments in biological standardization, vol. 104, Development and Clinical Progress of DNA vaccines, Brown, F., et al., eds., Basel, Karger, pp. 159-164 (Jul. 2000).

Barnfield, C. et al.,"The cellular basis of immune induction at mucosal surfaces by DNA vaccination," International Conference: Development and clinical progress of DNA vaccines, p. 28b (Oct. 1999).

Wheeler, C. J. et al, "A novel cationic lipid greatly enhances plasmid DNA delivery and expression in mouse lung," Proc. Natl Acad. Sci. USA 93:11454-11459, The National Academy of Sciences of the United States of America (1996).

Wang, B., at al., "Mucosal immunization with a DNA vaccine induces immune responses against HIV-1 at a mucosal site," Vaccine 15:821-825, Elsevier Science Ltd. (1997).

Wheeler, C. J. at al., "Converting an alcohol to an amine in a cationic lipid dramatically alters the co-lipid requirement, cellular transfection activity and the ultra structure of DNA-cytofectin complexes," Biochimica et Biophysica Acta 1280:1-11, Elsevier Science B. V. (1996).

Wheeler, C. J., "Adjuvant compositions and methods for enhancing immune responses to polynucleotide-based vaccines," Chem. Abstracts 133:636-637, Abs. No. 133:280556a, American Chemical Society (Nov. 2000).

Yasutomi, Y. et al., "A Vaccine-Elicited, Single Viral Epitope-Specific Cytotoxic T Lymphocyte Response Does Not Protect against Intravenous, Cell-Free Simian Immunodeficiency Virus Challenge," J. Virol. 69:2279-2284, American Society for Microbiology (1995).

Yokoyama, M. et al., "DNA immunization: Effects of vehicle and route of administration on the induction of protective antiviral immunity," FEMS Immunol. Med. Microbiol. 14:221-230, Elsevier Science B. V. (1996).

Boyer, J.D., et al., "Protection of chimpanzees from high-dose heterologous HIV-1 challenge by DNA vaccination," Nature Medicine 3:526-532, Nature Publishing Co (1997).

Fox, J. L., "No winner against AIDS," BioTechnology 12:128, Nature Publishing Co. (1994).

Klavinskis, L. S et al., "Intranasal immunization with Plasmid DNA-Lipid complexes elicits mucosal immunity in the female genital and rectal tracts," J. Immunol. 162:254-262, American Association of Immunologists (Jan. 1999).

"C35H71N2O2," Chem. Abstracts 133(Formula Index): 5164F, American Chemical Society (Dec. 2000).

Boyer, J.D. et al., "Protection of chimpanzees from high-dose heterologous HIV-1 challenge by DNA vaccination," Nature Medicine 3:526-532, Nature Publishing Company (1997).

Davis, H.L., et al., "DNA-based immunization against hepatitis B surfaces antigen (HBsAG) in normal and HBsAg-transgenic mice," Vaccines 15:849-852, Elsevier Science Ltd. (1997).

Debruyne, L.A. et al. ,"Lipid-mediated gene transfer of viral IL-10 prolongs vascularized cardiac allograft survival by inhibiting donor-specific cellular and humoral immune responses, "Gene Ther. 5:1079-1087 (Aug. 1998).

Donnelly, J., et al., "Adjuvant Effects of DNA vaccines, " Vaccines 97, Cold Spring Harbor Laboratory Press, pp. 105-111 (1997).

D'Souza, S., "Improved tuberculosis DNA vaccines by formulation in cationic lipids, "Infect. Immun. 70:3681-3688, American Society for Microbiology (Jul. 2002).

Ewert, K., et al., "Cationic Lipid-DNA complexes for gene therapy: understanding the relationship between complex structure and gene delivery pathways at the molecular level," Curr. Med. Chem. 11:133-149, Bentham Science Publishers (2004).

Etchart, N. et al., "Class I-restricted CTL induction by mucosal immunization with naked DNA encoding measles virus haemagglutinin,"J. Gen. Virol. 78:1577-1580, Science for General Microbiology (1997).

Felgner, P.L. et al., "Lipofection: A highly efficient, lipid-mediated DNA-transfection procedure," Proc. Natl. Acad. Sci. USA 84:7413-7414, The National Academy of Sciences of the United States of America (1987).

Felgner, J. H., et al., "Enhanced gene delivery and mechanism studies with a novel series of cationic lipid formulations" J. Biol. Chem. 269:2550-2561, The American Society for Biochemistry and Molecular Biology, Inc. (1994).

Felgner, P. L. et al.," Nonviral strategies for gene therapy," Sci. Am. 276:102-106, Scientific American, Inc. (1997).

Golding, B. et al.,"The potential for recruiting immune responses toward type 1 or type 2 T cell help," Am. J. Trop. Med. Hyg. 50:33-40, The American Society of tropical Medicine and Hygiene (1994).

Goncalves, M.A.F.V., "Concise peer into the background, initial thoughts and practices of human gene therapy," Bioessays 27:506-517, Wiley (2005).

Gramzinski, R. A. et al., "Immune response to a Hepatitis B DNA vaccine in Aotus monkeys: A comparison of vaccine formulation, route and method of administration," Mol. Med. 4:109-118, The Picower institute press (Feb. 1998).

* cited by examiner

| Plasmid | Leader | Gene | Promoter | Enhancer | Intron | Terminator |
|---|---|---|---|---|---|---|
| VR4700 | tissue plasminigen activator | influenza A/PR/8/34 nucleoprotein | CMV | CMV | CMV-A | mRBG |
| VR5900 | hen egg lysozyme | hen egg lysozyme | CMV | CMV | CMV-A | mRBG |
| VR1412 | not secreted | E. coli Lac Z | CMV | CMV | CMV-A | BGH |
| VR1623 | mouse immunoglobulin | mouse Id/humanFc | CMV | CMV | CMV-A | BGH |
| VR1904 | human factor IX | human factor IX | CMV | CMV | CMV-A | BGH |

FIG. 1

CYTOFECTIN STRUCTURES
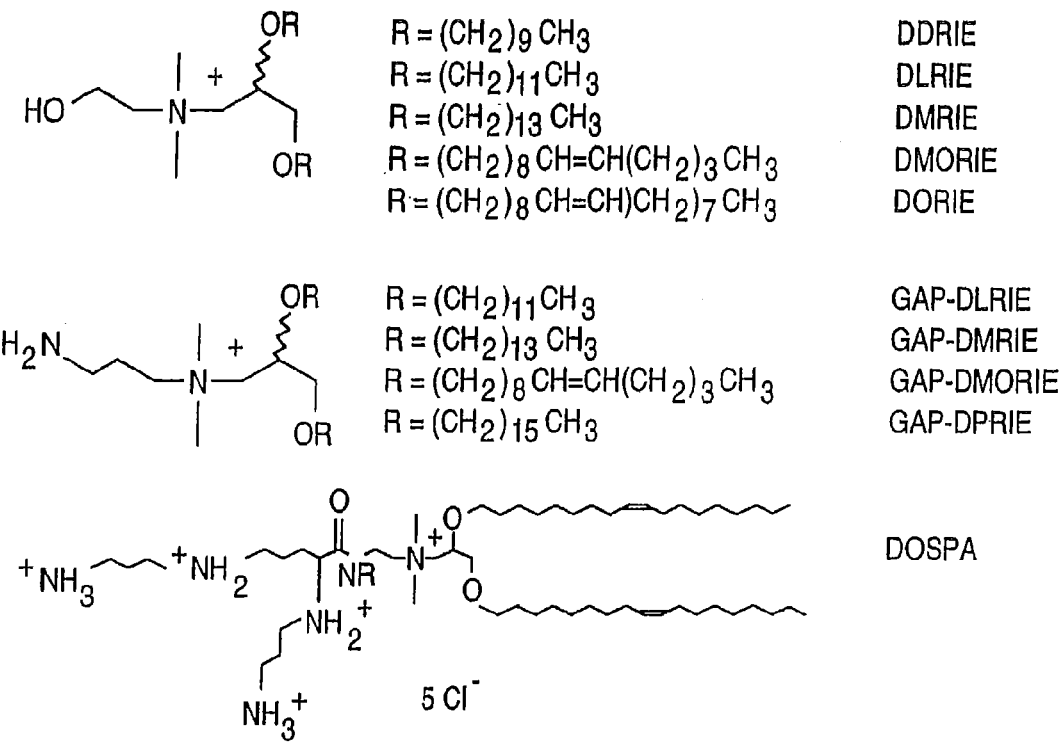
| | |
|---|---|
| R = $(CH_2)_9 CH_3$ | DDRIE |
| R = $(CH_2)_{11} CH_3$ | DLRIE |
| R = $(CH_2)_{13} CH_3$ | DMRIE |
| R = $(CH_2)_8 CH=CH(CH_2)_3 CH_3$ | DMORIE |
| R = $(CH_2)_8 CH=CH)CH_2)_7 CH_3$ | DORIE |
| | |
|---|---|
| R = $(CH_2)_{11} CH_3$ | GAP-DLRIE |
| R = $(CH_2)_{13} CH_3$ | GAP-DMRIE |
| R = $(CH_2)_8 CH=CH(CH_2)_3 CH_3$ | GAP-DMORIE |
| R = $(CH_2)_{15} CH_3$ | GAP-DPRIE |
DOSPA
CO-LIPID STRUCTURES
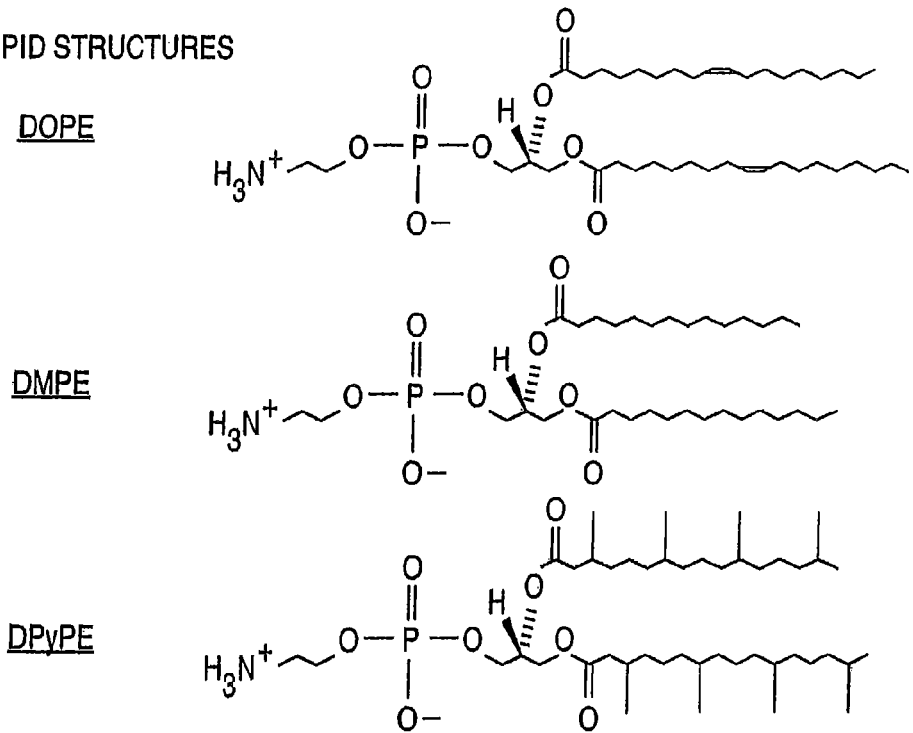
DOPE
DMPE
DPyPE
FIG. 2

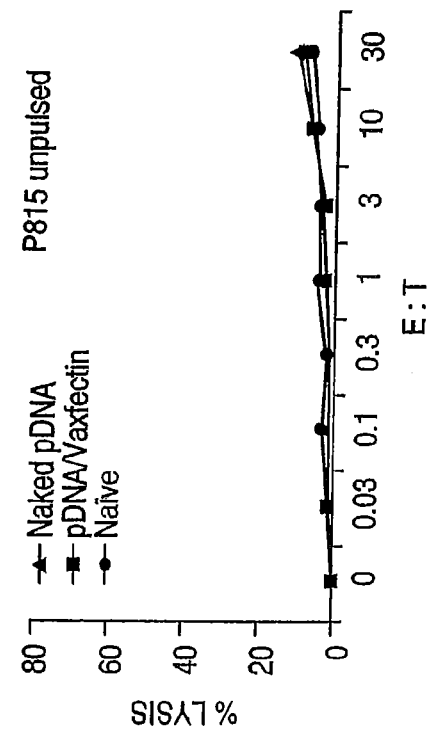
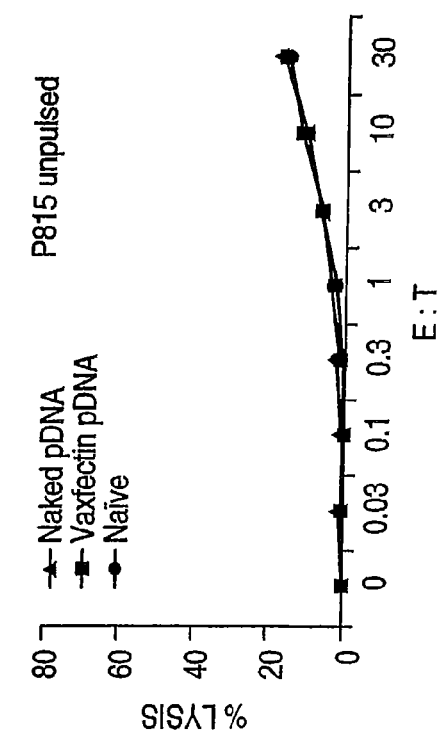
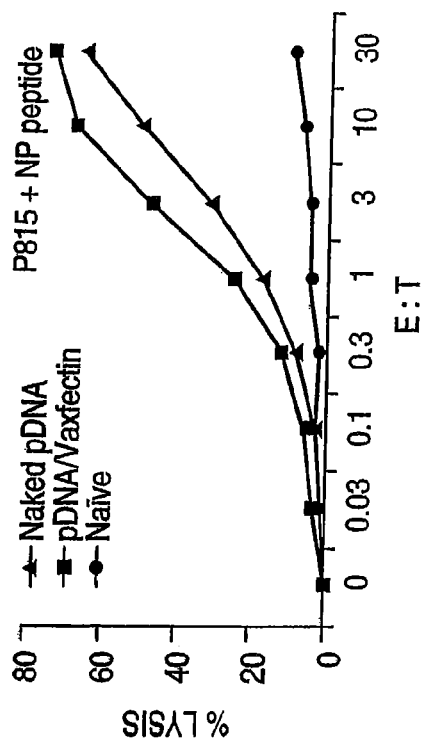
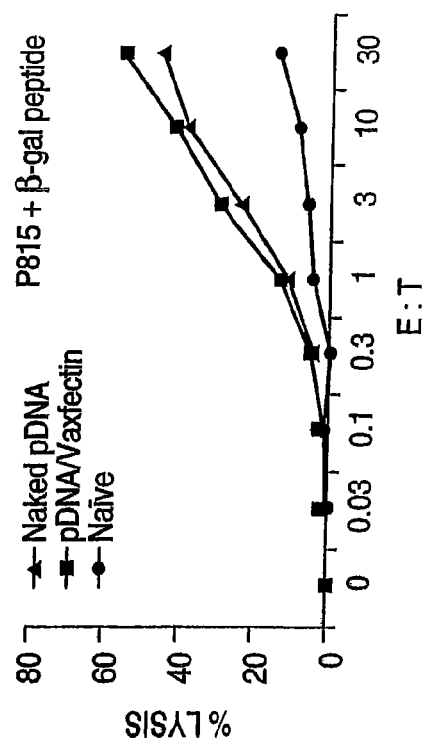
FIG. 12A
FIG. 12B
FIG. 12C
FIG. 12D

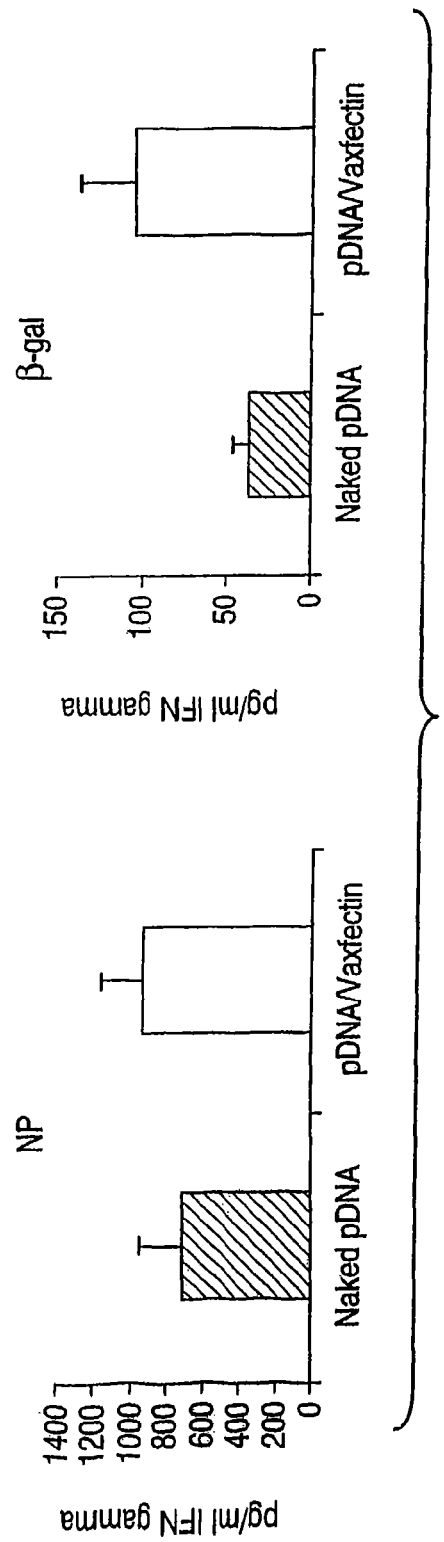
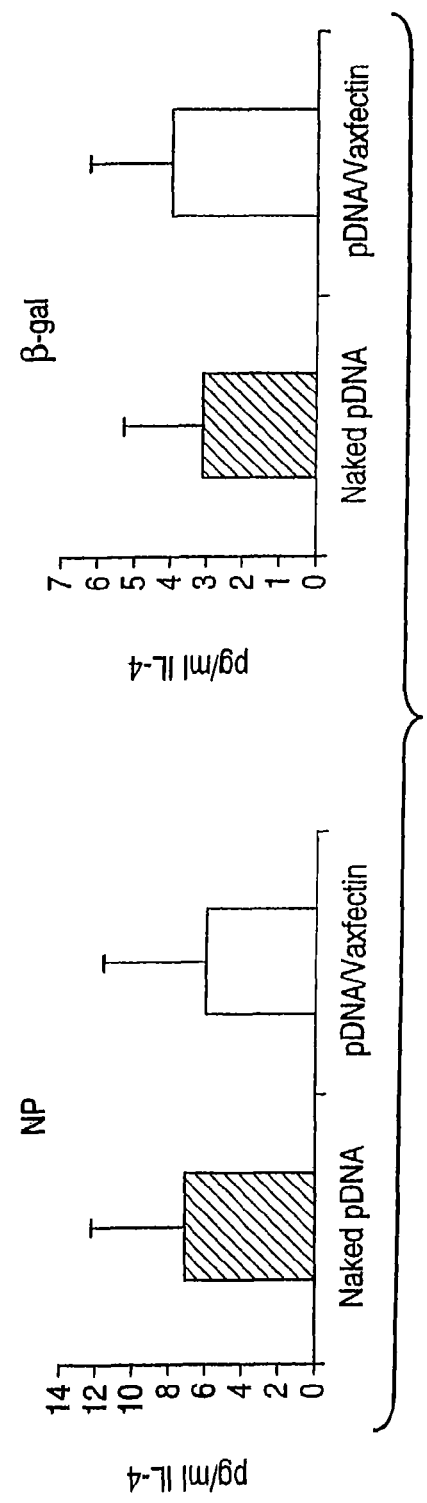
FIG. 14A
FIG. 14B

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: NP147-155 peptide

<400> SEQUENCE: 1

Thr Tyr Gln Arg Thr Arg Ala Leu Val
1               5

<210> SEQ ID NO 2
<211> LENGTH: 9
<212> TYPE: PRT
<213> ORGANISM: Artificial Sequence
<220> FEATURE:
<223> OTHER INFORMATION: Beta-gal876-884 peptide

<400> SEQUENCE: 2

Thr Pro His Pro Ala Arg Ile Gly Leu
1               5
```

ADJUVANT COMPOSITIONS AND METHODS FOR ENHANCING IMMUNE RESPONSES TO POLYNUCLEOTIDE-BASED VACCINES

CROSS REFERENCE TO RELATED APPLICATIONS

This application is a divisional application of U.S. Application Ser. No. 11/889,980, filed Aug. 17, 2007, which is a continuation application of U.S. application Ser. No. 10/391,216, filed Mar. 19, 2003 (now U.S. Pat. No. 7,582,613, issued on Sep. 1, 2009), which is a divisional application of U.S. application Ser. No. 09/534,943, filed Mar. 24, 2000 (now U.S. Pat. No. 6,586,409, issued on Jul. 1, 2003), which claims the benefit of U.S. Provisional Application No. 60/126,340, filed Mar. 26, 1999; said U.S. application Ser. No. 10/391,216 is also a continuation of U.S. application Ser. No. 09/937,604, filed Sep. 26, 2001 (now U.S. Pat. No. 7,105,574, issued on Sep. 12, 2006), which is a 35 U.S.C. §371 National Phase filing of International Application No. PCT/US00/08282, with an international filing date of Mar. 24, 2000, which claims the benefit of said U.S. Provisional Application No. 60/126,340; said U.S. application Ser. No. 09/937,604 is also a continuation of said U.S. application Ser. No. 09/534,943, which claims the benefit of said U.S. Provisional Application No. 60/126,340; each of the above applications is incorporated herein by reference in its entirety.

BACKGROUND OF THE INVENTION

Field of the Invention

The present invention relates generally to adjuvants, immunogenic compositions, and methods useful for polynucleotide-based vaccination. The present invention provides compositions and methods useful for enhancing immune response, especially the humoral immune response of vertebrates to polynucleotide-based vaccines. In particular, the present invention provides an adjuvant of cytofectin:co-lipid mixture wherein the cytofectin is (±)-N-(3-aminopropyl)-N,N-dimethyl-2,3-bis(syn-9-tetradeceneyloxy)-1-propanaminium bromide (GAP-DMORIE).

In the late 1980s, it was discovered that direct intramuscular (i.m.) injection of lipid-DNA complexes results in measurable protein expression, and that "naked" plasmid DNA (pDNA) is taken up and expressed in muscle to a greater extent than lipid-DNA complexes (Felgner, *Scientific American*, 276(6), 102-106 (1997)).

One of the first applications of pDNA injection technology was the induction of an immune response. In 1991, it was first reported that mice could be immunized against HIV gp120 by i.m. vaccination with gp120 plasmid DNA (Felgner et al., *Nature*, 349, 351-352 (1991)), and that mice could be protected from a lethal challenge of influenza virus after DNA immunization with influenza nucleoprotein (NP) antigen. Protection obtained after immunization with the highly conserved NP antigen extended across 2 different viral strains (Ulmer et al., *Current Opinions In Immunology*, 8, 531-536 (1996)). Numerous publications in the field of polynucleotide-based vaccination followed thereafter (e.g., Boyer et al., *J. Med. Primatology*, 25(3), 242-250 (1996); Boyer et al., *Nature Medicine*, 3(5), 526-532 (1997); Davis et al., Vaccine, 15(8), 849-852 (1997); Wang et al., *Vaccine*, 15(8), 821-825 (1997); Agadjanyan et al., *Current Topics In Microbiology And Immunology*, 226, 175-192 (1998); Heppell et al., *Fish & Shellfish Immunology*, 8(4), 271-286 (1998); Lodmell et al., *Nature Medicine*, 4(8), 949-952 (1998); Vanderzanden et al., *Virology*, 246(1), 134-144 (1998)).

A major problem frequently encountered in the course of polynucleotide-based vaccination is insufficient or suboptimal humoral response. Often, the antigens or immunogens encoded by the polynucleotide are expressed in vivo, but they are not sufficiently immunogenic to raise the antibody titer in the organism to sufficient levels to provide protection against subsequent challenge and/or to maintain the potential for generating therapeutically active antibody levels over extended time periods. To obtain a stronger humoral and/or cellular response, it is common to administer such vaccines in an immunogenic composition containing an adjuvant, a material which enhances the immune response of the patient to the vaccine. Adjuvants are useful generally for improving the immune response of an organism to a particular immunogen and are commonly included in vaccine compositions to increase the amount of antibodies produced and/or to reduce the quantity of immunogen and the frequency of administration.

A variety of adjuvants have been reported to effect differing levels of immune response enhancement to polynucleotide-based vaccination. Examples of such adjuvant materials include semi-synthetic bacterial cell wall-derived monophosphoryl lipid A (Sasaki, S., et al., *Infection and Immunity* 65(9), 3250-3258 (1997)), small molecule immunostimulators (Sasaki, S., et al., *Clin. Exp. Immunol.* 111, 30-35 (1998)), and saponins (Sasaki, S., et al., *J. Virology* 72(6), 4391-4939 (1998)). The immune response from i.m. pDNA vaccination has also been enhanced through the use of cationic lipids (Ishii, N., et al., *Aids Res. Hum. Retroviruses* 13(16), 1421-1428 (1997)), Okada, E., et al., *J. Immunology* 159, 3638-3647 (1997); Yokoyama, M., et al., *FEMS Immunol. Med. Microbiol.* 14, 221-230 (1996); Gregoriadis, G., et al., *FEBS Letters* 402, 107-110 (1997); Gramzinski, R. A., et al., *Molecular Medicine* 4, 109-118 (1998); Klavinskis, L. S., et al., *Vaccine* 15(8), 818-820 (1997); Klavinskis, L. S., et al., *J. Immunology* 162, 254-262 (1999); Etchart, N., et al., *J. Gen. Virology* 78, 1577-1580 (1997); Norman, J., et al., in *Methods in Molecular Medicine, Vol. 9; DNA Vaccines: Methods and Protocols*, D. B. Lowrie and R. Whalen, eds., Chapter 16, pp. 185-196 (1999)). Cationic lipids were originally studied as cytofectins to enhance delivery of pDNA into cells in vitro; however, further development has led to successful specific applications of protein delivery in vivo (Wheeler, C. J., et al., *Proc. Natl. Acad. Sci. USA* 93, 11454-11459 (1996); Stephan, D. J., et al., *Human Gene Therapy* 7, 1803-1812 (1996); DeBruyne, L. A., et al., *Gene Therapy* 5, 1079-1087 (1998)). Accordingly, such cytofectins may be useful for vaccine applications by enhancing delivery of the pDNA into the cells responsible for giving rise to the humoral arm of the immune response, thereby increasing antibody titer levels.

Commonly used adjuvants show low levels of immune response enhancement for vaccination (typically less than 3-fold) and possess undesirable toxicological and manufacturing profiles. In addition, cationic lipids used previously for vaccination show only low levels of humoral enhancement. There is a need for more adjuvant compositions useful for enhancing the immune response of vertebrates to immunization, especially to pDNA vaccination.

BRIEF SUMMARY OF THE INVENTION

The present invention is directed to adjuvant and immunogenic compositions and to methods for the polynucleotide-based vaccination of a vertebrate, to help protect the vertebrate from a disease, to treat a diseased vertebrate, or both. In certain preferred embodiments, the present invention is directed to a method for immunizing a vertebrate by administering to the vertebrate a composition comprising a polynucleotide that encodes for an immunogen, wherein the polynucleotide is complexed with an adjuvant composition comprising GAP-DMORIE. Preferably, the composition may comprise one or more co-lipids. The immunogen-encoding polynucleotide, upon incorporation into the cells of the vertebrate, produces an immunologically effective amount of an immunogen (e.g., an immunogenic protein). The adjuvant composition of the present invention enhances the immune response of the vertebrate to the immunogen.

One aspect of the present invention is an adjuvant composition comprising a mixture of one or more cytofectins and one or more co-lipids, which adjuvant composition is useful for enhancing the humoral immune response of a vertebrate to an immunogen. Preferably, the adjuvant composition includes the cytofectin GAP-DMORIE and one or more co-lipids. Preferably also, the co-lipid is a neutral lipid such as, for example, a phosphatidylethanolamine. More preferably, the co-lipid is 1,2-dioleoyl-sn-glycero-3-phosphoethanolamine (DOPE), 1,2-diphytanoyl-sn-glycero-3-phosphoethanolamine (DPyPE), and/or 1,2-dimyristoyl-glycer-3-phosphoethanolamine (DMPE). Most preferably, the co-lipid is DPyPE.

Another aspect of the present invention is an immunogenic composition comprising one or more immunogens and an adjuvant composition comprising the cytofectin GAP-DMORIE and one or more co-lipids. In certain embodiments, the source of the immunogen is an immunogen-encoding polynucleotide, such as in the case of a pDNA vaccine. Preferably, in those embodiments, the pDNA or polynucleotide is complexed with an adjuvant composition comprising GAP-DMORIE and one or more co-lipids.

Another aspect of the present invention is a method for immunizing a vertebrate by administering to the vertebrate an immunogenic composition comprising a complex of one or more immunogen-encoding polynucleotides and GAP-DMORIE in an amount sufficient to generate an immune response to the encoded immunogen. Preferably, the immunogenic composition further includes one or more co-lipids such as, for example, DOPE and/or DPyPE. Most preferably, the co-lipid is DPyPE.

The present invention, in contrast to the prior art, is useful for enhancing the humoral immune response of a vertebrate to a polynucleotide-based vaccine, through the use of GAP-DMORIE. Elevation of antibody levels is particularly advantageous in applications where antibody levels from the immunogen-encoding polynucleotide alone are sub-optimal. In a related advantage, if the desired level of antibodies is produced with a given dose of pDNA, the amount of pDNA necessary to reach the predetermined antibody titer level can be reached using a lower pDNA dose. For pDNA vaccination applications, this advantage is important because acceptable vaccination volumes, coupled with functional limits on the concentration of pDNA, define an upper limit on a given vaccine dose. This advantage is particularly beneficial for vaccines containing multiple plasmids, each of which must be present in sufficient quantity to elicit an immune response to its particular transgene.

BRIEF DESCRIPTION OF THE FIGURES

The foregoing aspects and advantages of the present invention will be readily apparent to one skilled in the art upon reference to the figures and the detailed description which follows.

FIG. 1 illustrates the diagrams of Plasmid DNAs. Each vector has a pUC19 origin of replication and a kanamycin resistance gene for plasmid growth in *E. coli* bacteria. CMV=human cytomegalovirus promoter and enhancer; CMV-A=human cytomegalovirus intron A; mRGB=modified rabbit β-globin polyadenylation signal; BGH=bovine growth hormone polyadenylation signal.

FIG. 2 illustrates the chemical structures for the cytofectin GAP-DMORIE and the co-lipids DOPE and DPyPE, along with structurally related cytofectins.

FIGS. 12A, 12B, 12C, and 12D illustrate that immunization with pDNA formulated with cytofectin induces antigen specific CTL lysis of target cells coated with antigen derived peptides. BALB/c mice were immunized with injections of 5 µg pDNA+/−Vaxfectin into each rectus femoris muscle at 0 and 3 weeks. Spleens were harvested 11-12 weeks following the initial immunizations and stimulated for 5-6 days with 1 µM $NP_{147\text{-}155}$ or $\beta\text{-gal}_{876\text{-}884}$ peptide and 0.5 U/ml of recombinant murine IL-2. Data presented are the average % lysis for 5 spleens in each group. Similar results were obtained in a second assay for both NP and β-gal specific CTL. A) P815 target cells pulsed with $NP_{147\text{-}155}$ peptide; B) Unpulsed P815 target cells; C) P815 target cells pulsed with $\beta\text{-gal}_{876\text{-}884}$ peptide; D) Unpulsed P815 target cells.

FIGS. 14A and 14B illustrate Th1 type cytokine secretion profiles of splenocytes from pDNA/Vaxfectin immunized mice. Spleens were harvested 11-12 weeks following the initial immunizations and were stimulated for 72 hours with 5 µg/ml of purified NP or β-gal protein. IFN-γ and IL-4 in culture supernatants were determined by ELISA. The data presented are the average concentration of cytokine from cultures of stimulated splenocytes less the concentration of cytokine from cultures of unstimulated splenocytes (+/−SEM). A) Antigen specific IFN-γ response of splenocytes from naked pDNA and pDNA/cytofectin immunized mice (n=10 for each group). B) Antigen specific IL-4 response of splenocytes from naked pDNA and pDNA/Vaxfectin immunized mice (n=10 for each group).

DETAILED DESCRIPTION OF THE INVENTION

It will be apparent to one skilled in the art, in view of the following detailed description and the claims appended hereto, that various substitutions and modifications may be made to the present invention without departing from the scope of the invention as claimed.

The present invention is directed to the polynucleotide-based immunization of a vertebrate, to protect from or treat a vertebrate with a disease condition. The present invention includes the use of cytofectin, especially GAP-DMORIE in adjuvants, immunogenic compositions, and methods for immunizing a vertebrate, especially with polynucleotude-based immunogen.

The adjuvant composition of the present invention includes one or more cytofectins and, in preferred embodiments, one or more co-lipids. Cytofectins are cationic lipids. In one embodiment, cytofectin is GAP-DMORIE, which has a structure corresponding to a 2,3-dialkoxy-propanaminium skeleton possessing a unique combination of two linear fourteen-carbon mono-unsaturated alkyl chains and a propylamine substituent on the quaternary nitrogen (See FIG. 2).

Figure 3:
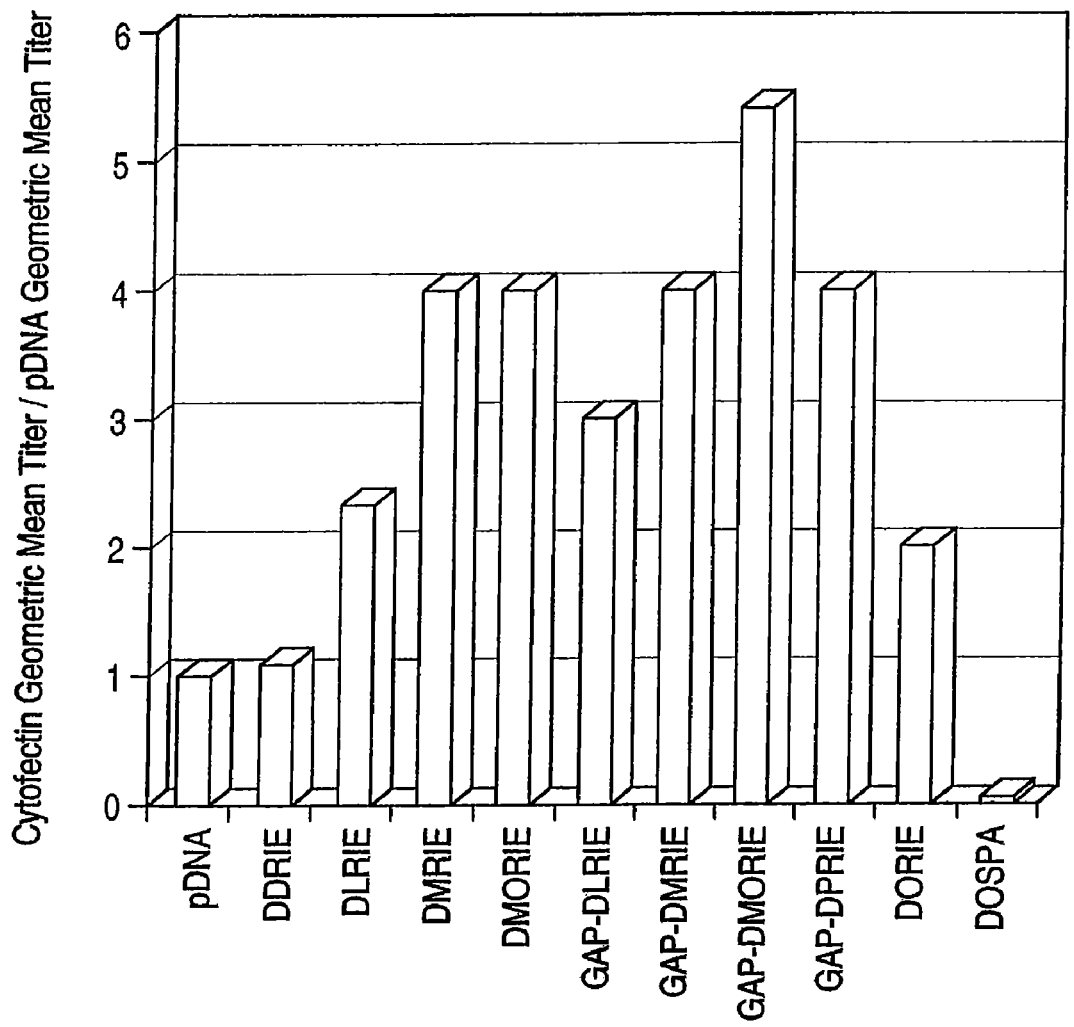
FIG. 3 is a bar graph demonstrating that the structural elements of cytofectins determine the level of antibody stimulation upon administration. Mice were immunized using pDNA coding for influenza nuclear protein (NP), complexed with various cytofectins (identified on the horizontal axis) formulated as a 1:1 (mol:mol) mixture with DOPE co-lipid. Each animal in the test group (five animals per group) was injected at day "0" and at 3 weeks (boost injection) with 5 μg pDNA in 50 μl physiological saline per leg in the rectus femoris muscle, either alone or as a complex with a cytofectin:co-lipid adjuvant. After 6 weeks (3 weeks after the boost), serum was removed from the animals and the NP antibody titers were determined by serial dilution using an ELISA assay. Cytofectin:co-lipid enhancement was evaluated using the ratio of (i) the geometric mean titer (GMT) from a cytofectin-augmented transfection group to (ii) the GMT from pDNA transfection alone, using an equivalent control group of animals.

GAP-DMORIE contains a set of synergistic structural features, none of which when individually incorporated into the skeleton affords optimal activity. Thus, with reference to FIG. 3, by examining the group DMRIE ((±)-N-(2-hydroxyethyl)-N,N-dimethyl-2,3-bis(tetradecyloxy)-1-propanaminium bromide), DLRIE ((±)-N-(2-hydroxyethyl)-N,N-dimethyl-2,3-bis(dodecyloxy)-1-propanaminium bromide) and DDRIE ((±)-N-(2-hydroxyethyl)-N,N-dimethyl-2,3-bis(decyloxy)-1-propanaminium bromide), and comparing the group GAP-DMRIE ((±)-N-(3-aminopropyl)-N,N-dimethyl-2,3-(bis-tetradecyloxy)-1-propanaminium bromide), GAP-DLRIE ((±)-N-(3-aminopropyl)-N,N-dimethyl-2,3-(bis-dodecyloxy)-1- propanaminium bromide), and GAP-DPRIE ((±)-N-(3-aminopropyl)-N,N-dimethyl-2,3-(bis-hexadecyloxy)-1-propanaminium bromide), it is evident that fourteen-carbon chains are more active (i.e., elicit greater levels of antibody stimulation) relative to other chain lengths, whether the quaternary nitrogen is substituted with a hydroxyethyl moiety (former group) or with a propylamino moiety (latter group). By comparing DMRIE versus GAP-DMRIE (see FIG. 3), it appears that incorporating a propylamino group in lieu of a hydroxyethyl group offers no apparent advantage. Similarly, DMRIE and DMORIE are equally active despite the incorporation of an olefin into the fourteen-carbon chain. However, by incorporating the combination of a propylamino substituent and an olefin moiety, GAP-DMORIE appears to be more active than either DMORIE or GAP-DMRIE, based on the geometric mean titer (GMT) relative to that for pDNA alone (FIG. 3). In addition, DOSPA (2,3-dioleyloxy-N-(2-(sperminecarboxamido)ethyl)-N,N-dimethyl-1-propanaminium pentahydrochloride), which incorporates both an olefin into its eighteen-carbon alkyl chains and an amino-bearing quaternary ammonium substituent, is not only less active than DORIE ((±)-N-(2-hydroxyethyl)-N,N-dimethyl-2,3-bis(syn-9-octadeceneyloxy)-1-propanaminium bromide), which is equivalent except for quaternary ammonium substitution, but dramatically decreases the level of antibody titers relative to those seen for pDNA alone. The preferred salt of GAP-DMORIE for use in the present invention is the bromide salt; however, all suitable salts of GAP-DMORIE are encompassed by the term "GAP-DMORIE."

For purposes of definition, the term "co-lipid" refers to any hydrophobic material that can be combined with the cytofectin component, e.g., GAP-DMORIE. The co-lipid of the present invention can be amphipathic lipids and neutral lipids. Amphipathic lipids include phospholipids, e.g., phosphatidylethanolamines and phosphatidylcholines. Neutral lipids include cholesterol. In one preferred embodiment, phosphatidylethanolamines include DOPE, DMPE, and DPyPE. DOPE and DPyPE are particularly preferred; the most preferred co-lipid is DPyPE, which comprises two phytanoyl substituents incorporated into the diacylphosphatidylethanolamine skeleton. As illustrated by FIG. 3, the combination of the cytofectin GAP-DMORIE with the co-lipid DPyPE results in a synergistic effect to further enhance the humoral immune response, as evidenced by the level of antibody titers from pDNA immunization.

According to the present invention, cytofectins and co-lipids may be mixed or combined in a number of ways to produce a variety of adjuvant compositions of non-covalently bonded macroscopic structures, e.g., liposomes, multilamellar vesicles, unilamellar vesicles, micelles, and simple films. The cytofectins and co-lipids can be mixed in a variety of molar ratios. Preferably, the molar ratio of GAP-DMORIE and co-lipid is from about 9:1 to about 1:9, more preferably, the molar ratio is from about 4:1 to about 1:4, or from about 2:1 to about 1:2. Most preferably, the molar ratio is about 1:1.

The cytofectins and co-lipids can be dissolved in a solvent to increase homogenity of the mixture. Suitable solvents include chloroform. For example, GAP-DMORIE can be mixed with one or more co-lipids in chloroform. For example, GAP-DMORIE can be mixed with one or more co-lipids in chloroform, the mixture is subsequently evaporated under vacuum to form a dried thin layer of film on the inner surface of a glass vessel, e.g., a Rotovap round-bottomed flask. Such dried mixture can be suspended in an aqueous solvent where the amphipathic lipid component molecules self-assemble into homogenous lipid vesicles. These lipid vesicles can subsequently be processed by any methods used in the art to have a selected mean diameter of uniform size prior to complexing with other entities, e.g., pDNA. The sonication of a lipid solution is described in Felgner et al., *Proc. Natl. Acad. Set. USA* 84, 7413-7417 (1987) and in U.S. Pat. No. 5,264,618, the disclosure of which is incorporated herein by reference.

The adjuvant compositions of the present invention may include additives such as hydrophobic and amphiphilic additives. For example, the adjuvant composition can include sterols, fatty acids, gangliosides, glycolipids, lipopeptides, liposaccharides, neobees, niosomes, prostaglandins or sphingolipids. The amount of additives included in the adjuvant may be any including from about 0.1 mol % to about 99.9 mol %, from about 1 mol % to about 50 mol %, and from about 2 mol % to about 25 mol %, relative to total amount of lipid. These additives can also be included in an immunogenic composition containing the adjuvant composition of the present invention.

The immunogenic composition of the present invention includes an adjuvant composition as described above and an immunogen. An "immunogen" is meant to encompass any antigenic or immunogenic polypeptides including poly-aminoacid materials having epitopes or combinations of epitopes, and immunogen-encoding polynucleotides. In addition, an "immunogen" is also meant to encompass any poly-saccharide material useful in generating immune response. As used herein, an antigenic polypeptide or an immunogenic polypeptide is a polypeptide which, when introduced into a vertebrate, reacts with the immune system molecules of the vertebrate, i.e., is antigenic, and/or induces an immune response in the vertebrate, i.e., is immunogenic. It is quite likely that an immunogenic polypeptide will also be antigenic, but an antigenic polypeptide, because of its size or conformation, may not necessarily be immunogenic. Examples of antigenic and immunogenic polypeptides include, but are not limited to, polypeptides from infectious agents such as bacteria, viruses, parasites, or fungi, allergens such as those from pet dander, plants, dust, and other environmental sources, as well as certain self polypeptides, for example, tumor-associated antigens.

Antigenic and immunogenic polypeptides of the present invention can be used to prevent or treat, i.e., cure, ameliorate, lessen the severity of, or prevent or reduce contagion of viral, bacterial, fungal, and parasitic infectious diseases, as well as to treat allergies.

In addition, antigenic and immunogenic polypeptides of the present invention can be used to prevent or treat, i.e., cure, ameliorate, or lessen the severity of cancer including, but not limited to, cancers of oral cavity and pharynx (i.e., tongue, mouth, pharynx), digestive system (i.e., esophagus, stomach, small intestine, colon, rectum, anus, anal canal, anorectum, liver, gallbladder, pancreas), respiratory system (i.e., larynx, lung), bones, joints, soft tissues (including heart), skin, melanoma, breast, reproductive organs (i.e., cervix, endometrium, ovary, vulva, vagina, prostate, testis, penis), urinary system (i.e., urinary bladder, kidney, ureter, and other urinary organs), eye, brain, endocrine system (i.e., thyroid and other endocrine), lymphoma (i.e., hodgkin's disease, non-hodgkin's lymphoma), multiple myeloma, leukemia (i.e., acute lymphocytic leukemia, chronic lymphocytic leukemia, acute myeloid leukemia, chronic myeloid leukemia).

Examples of viral antigenic and immunogenic polypeptides include, but are not limited to, adenovirus polypeptides, alphavirus polypeptides, calicivirus polypeptides, e.g., a calicivirus capsid antigen, coronavirus polypeptides, distemper virus polypeptides, Ebola virus polypeptides, enterovirus polypeptides, flavivirus polypeptides, hepatitis virus (AE) polypeptides, e.g., a hepatitis B core or surface antigen, herpesvirus polypeptides, e.g., a herpes simplex virus or varicella zoster virus glycoprotein, immunodeficiency virus polypeptides, e.g., the human immunodeficiency virus envelope or protease, infectious peritonitis virus polypeptides, influenza virus polypeptides, e.g., an influenza A hemagglutinin, neuraminidase, or nucleoprotein, leukemia virus polypeptides, Marburg virus polypeptides, orthomyxovirus polypeptides, papilloma virus polypeptides, parainfluenza virus polypeptides, e.g., the hemagglutinin/neuraminidase, paramyxovirus polypeptides, parvovirus polypeptides, pestivirus polypeptides, picorna virus polypeptides, e.g., a poliovirus capsid polypeptide, pox virus polypeptides, e.g., a vaccinia virus polypeptide, rabies virus polypeptides, e.g., a rabies virus glycoprotein G, reovirus polypeptides, retrovirus polypeptides, and rotavirus polypeptides.

Examples of bacterial antigenic and immunogenic polypeptides include, but are not limited to, *Actinomyces* polypeptides, *Bacillus* polypeptides, *Bacteroides* polypeptides, *Bordetella* polypeptides, *Bartonella* polypeptides, *Borrelia* polypeptides, e.g., *B. burgdorferi* OspA, *Brucella* polypeptides, *Campylobacter* polypeptides, *Capnocytophaga* polypeptides, *Chlamydia* polypeptides, *Clostridium* polypeptides, *Corynebacterium* polypeptides, *Coxiella* polypeptides, *Dermatophilus* polypeptides, *Enterococcus* polypeptides, *Ehrlichia* polypeptides, *Escherichia* polypeptides, *Francisella* polypeptides, *Fusobacterium* polypeptides, *Haemobartonella* polypeptides, *Haemophilus* polypeptides, e.g., *H. influenzae* type b outer membrane protein, *Helicobacter* polypeptides, *Klebsiella* polypeptides, L-form bacteria polypeptides, *Leptospira* polypeptides, *Listeria* polypeptides, *Mycobacteria* polypeptides, *Mycoplasma* polypeptides, *Neisseria* polypeptides, *Neorickettsia* polypeptides, *Nocardia* polypeptides, *Pasteurella* polypeptides, *Peptococcus* polypeptides, *Peptostreptococcus* polypeptides, *Pneumococcus* polypeptides, *Proteus* polypeptides, *Pseudomonas* polypeptides, *Rickettsia* polypeptides, *Rochalimaea* polypeptides, *Salmonella* polypeptides, *Shigella* polypeptides, *Staphylococcus* polypeptides, *Streptococcus* polypeptides, e.g., *S. pyogenes* M proteins, *Treponema* polypeptides, and *Yersinia* polypeptides, e.g., *Y. pestis* F1 and V antigens.

Examples of fungal immunogenic and antigenic polypeptides include, but are not limited to, *Absidia* polypeptides, *Acremonium* polypeptides, *Alternaria* polypeptides, *Aspergillus* polypeptides, *Basidiobolus* polypeptides, *Bipolaris* polypeptides, *Blastomyces* polypeptides, *Candida* polypeptides, *Coccidioides* polypeptides, *Conidiobolus* polypeptides, *Cryptococcus* polypeptides, *Curvalaria* polypeptides, *Epidermophyton* polypeptides, *Exophiala* polypeptides, *Geotrichum* polypeptides, *Histoplasma* polypeptides, *Madurella* polypeptides, *Malassezia* polypeptides, *Microsporum* polypeptides, *Moniliella* polypeptides, *Mortierella* polypeptides, *Mucor* polypeptides, *Paecilomyces* polypeptides, *Penicillium* polypeptides, *Phialemonium* polypeptides, *Phialophora* polypeptides, *Prototheca* polypeptides, *Pseudallescheria* polypeptides, *Pseudomicrodochium* polypeptides, *Pythium* polypeptides, *Rhinosporidium* polypeptides, *Rhizopus* polypeptides, *Scolecobasidium* polypeptides, *Sporothrix* polypeptides, *Stemphylium* polypeptides, *Trichophyton* polypeptides, *Trichosporon* polypeptides, and *Xylohypha* polypeptides.

Examples of protozoan parasite immunogenic and antigenic polypeptides include, but are not limited to, *Babesia* polypeptides, *Balantidium* polypeptides, *Besnoitia* polypeptides, *Cryptosporidium* polypeptides, *Eimeria* polypeptides, *Encephalitozoon* polypeptides, *Entamoeba* polypeptides, *Giardia* polypeptides, *Hammondia* polypeptides, *Hepatozoon* polypeptides, *Isospora* polypeptides, *Leishmania* polypeptides, *Microsporidia* polypeptides, *Neospora* polypeptides, *Nosema* polypeptides, *Pentatrichomonas* polypeptides, *Plasmodium* polypeptides, e.g., *P. falciparum* circumsporozoite (PfCSP), sporozoite surface protein 2 (PfSSP2), carboxyl terminus of liver state antigen 1 (PfLSA1 c-term), and exported protein 1 (PfExp-1), *Pneumocystis* polypeptides, *Sarcocystis* polypeptides, *Schistosoma* polypeptides, *Theileria* polypeptides, *Toxoplasma* polypeptides, and *Trypanosoma* polypeptides.

Examples of helminth parasite immunogenic and antigenic polypeptides include, but are not limited to, *Acanthocheilonema* polypeptides, *Aelurostrongylus* polypeptides, *Ancylostoma* polypeptides, *Angiostrongylus* polypeptides, *Ascaris* polypeptides, *Brugia* polypeptides, *Bunostomum* polypeptides, *Capillaria* polypeptides, *Chabertia* polypeptides, *Cooperia* polypeptides, *Crenosoma* polypeptides, *Dictyocaulus* polypeptides, *Dioctophyme* polypeptides, *Dipetalonema* polypeptides, *Diphyllobothrium* polypeptides, *Diplydium* polypeptides, *Dirofilaria* polypeptides, *Dracunculus* polypeptides, *Enterobius* polypeptides, *Filaroides* polypeptides, *Haemonchus* polypeptides, *Lagochilascaris* polypeptides, *Loa* polypeptides, *Mansonella* polypeptides, *Muellerius* polypeptides, *Nanophyetus* polypeptides, *Necator* polypeptides, *Nematodirus* polypeptides, *Oesophagostomum* polypeptides, *Onchocerca* polypeptides, *Opisthorchis* polypeptides, *Ostertagia* polypeptides, *Parafilaria* polypeptides, *Paragonimus* polypeptides, *Parascaris* polypeptides, *Physaloptera* polypeptides, *Protostrongylus* polypeptides, *Setaria* polypeptides, *Spirocerca* polypeptides *Spirometra* polypeptides, *Stephanofilaria* polypeptides, *Strongyloides* polypeptides, *Strongylus* polypeptides, *Thelazia* polypeptides, *Toxascaris* polypeptides, *Toxocara* polypeptides, *Trichinella* polypeptides, *Trichostrongylus* polypeptides, *Trichuris* polypeptides, *Uncinaria* polypeptides, and *Wuchereria* polypeptides.

Examples of ectoparasite immunogenic and antigenic polypeptides include, but are not limited to, polypeptides (including protective antigens as well as allergens) from fleas; ticks, including hard ticks and soft ticks; flies, such as midges, mosquitoes, sand flies, black flies, horse flies, horn flies, deer flies, tsetse flies, stable flies, myiasis-causing flies and biting gnats; ants; spiders, lice; mites; and true bugs, such as bed bugs and kissing bugs.

Examples of tumor-associated antigenic and immunogenic polypeptides include, but are not limited to, tumor-specific immunoglobulin variable regions, GM2, Tn, sTn, Thompson-Friedenreich antigen (TF), Globo H, Le(y), MUC1, MUC2, MUC3, MUC4, MUC5AC, MUC5B, MUC7, carcinoembryonic antigens, beta chain of human chorionic gonadotropin (hCG beta), HER2/neu, PSMA, EGFRvIII, KSA, PSA, PSCA, GP100, MAGE 1, MAGE 2, TRP 1, TRP 2, tyrosinase, MART-1, PAP, CEA, BAGE, MAGE, RAGE, and related proteins.

Also included as polypeptides of the present invention are fragments or variants of the foregoing polypeptides, and any combination of the foregoing polypeptides. Additional polypeptides may be found, for example in "Foundations in Microbiology," Talaro, et al., eds., McGraw-Hill Companies (October, 1998), Fields, et al., "Virology," 3d ed., Lippincott-Raven (1996), "Biochemistry and Molecular Biology of Parasites," Man, et al., eds., Academic Press (1995), and Deacon, J., "Modern Mycology," Blackwell Science Inc (1997), which are incorporated herein by reference.

The immunogen-encoding polynucleotide is intended to encompass a singular "polynucleotide" as well as plural "polynucleotides," and refers to an isolated molecule or construct. The immunogen-encoding polynucleotides include nucleotide sequences, nucleic acids, nucleic acid oligomers, messenger RNA (mRNA), DNA (e.g., pDNAs, derivatives of pDNA, linear DNA), or fragments of any of thereof. The immunogen-encoding polynucleotides may be provided in linear, circular, e.g., plasmid, or branched form as well as double-stranded or single-stranded form. The immunogen-encoding polynucleotides may comprise a conventional phosphodiester bond or a non-conventional bond, e.g., an amide bond, such as found in peptide nucleic acids (PNA).

According to the present invention, the immunogen-encoding polynucleotide can be part of a circular or linearized plasmid containing a non-infectious and non-integrating polynucleotide. A non-infectious polynucleotide is a polynucleotide that does not infect vertebrate cells while a non-integrating polynucleotide does not integrate into the genome of vertebrate cells. A linearized plasmid is a plasmid that was previously circular but has been linearized, for example, by digestion with a restriction endonuclease. The immunogen-encoding polynucleotide may comprise a sequence that directs the secretion of a polypeptide.

The form of immunogen-encoding polynucleotides depends in part on the desired kinetics and duration of expression. When long-term delivery of a protein encoded by a polynucleotide is desired, the preferred form is DNA. Alternatively, when short-term transgene protein delivery is desired, the preferred form is mRNA, since mRNA can be rapidly translated into polypeptide, however RNA may be degraded more quickly than DNA.

In one embodiment, the immunogen-encoding polynucleotide is RNA, e.g., messenger RNA (mRNA). Methods for introducing RNA sequences into mammalian cells is described in U.S. Pat. No. 5,580,859, the disclosure of which is incorporated herein by reference. A viral alphavector, a non-infectious vector useful for administering RNA, may be used to introduce RNA into mammalian cells. Methods for the in vivo introduction of alphaviral vectors to mammalian tissues are described in Altman-Hamamdzic, S., et al., *Gene Therapy* 4, 815-822 (1997), the disclosure of which is incorporated herein by reference.

Preferably, the immunogen-encoding polynucleotide is DNA. In the case of DNA, a promoter is preferably operably linked to the nucleotide sequence encoding for the immunogen. The promoter can be a cell-specific promoter that directs substantial transcription of the DNA only in predetermined cells. Other transcription control elements, besides a promoter, can be included with the polynucleotide to direct cell-specific transcription of the DNA. An operable linkage is a linkage in which a polynucleotide encoding for an immunogenic molecule is connected to one or more regulatory sequences in such a way as to place expression of the immunogen under the influence or control of the regulatory sequence(s). Two DNA sequences (such as a coding sequence and a promoter region sequence linked to the 5' end of the coding sequence) are operably linked if induction of promoter function results in the transcription of mRNA encoding for the desired immunogen and if the nature of the linkage between the two DNA sequences does not (1) result in the introduction of a frame-shift mutation, (2) interfere with the ability of the expression regulatory sequences to direct the expression of the immunogen, or (3) interfere with the ability of the DNA template to be transcribed. Thus, a promoter region would be operably linked to a DNA sequence if the promoter was capable of effecting transcription of that DNA sequence.

The immunogen-encoding polynucleotide, e.g., pDNA, mRNA, polynucleotide or nucleic acid oligomer can be solubilized in any of various buffers prior to mixing or complexing with the adjuvant components, e.g., cytofectins and co-lipids. Suitable buffers include phosphate buffered saline (PBS), normal saline, Tris buffer, and sodium phosphate. Insoluble polynucleotides can be solubilized in a weak acid or weak base, and then diluted to the desired volume with a buffer. The pH of the buffer may be adjusted as appropriate. In addition, a pharmaceutically acceptable additive can be used to provide an appropriate osmolarity. Such additives are within the purview of one skilled in the art.

According to the present invention, the immunogen-encoding polynucleotides can be complexed with the adjuvant compositions of the present invention by any means known in the art, e.g., by mixing a pDNA solution and a solution of cytofectin/co-lipid liposomes. In one embodiment, the concentration of each of the constituent solutions is adjusted prior to mixing such that the desired final pDNA/cytofectin: co-lipid ratio and the desired pDNA final concentration will be obtained upon mixing the two solutions. For example, if the desired final solution is to be physiological saline (0.9% weight/volume), both pDNA and cytofectin:co-lipid liposomes are prepared in 0.9% saline and then simply mixed to produce the desired complex. The cytofectin:co-lipid liposomes can be prepared by any means known in the art. For example, one can hydrate a thin film of GAP-DMORIE and co-lipid mixture in an appropriate volume of aqueous solvent by vortex mixing at ambient temperatures for about 1 minute. Preparation of a thin film of cytofectin and co-lipid mixture is known to a skilled artisan and can be prepared by any suitable techniques. For example, one can mix chloroform solutions of the individual components to generate an equimolar solute ratio and subsequently aliquot a desired volume of the solutions into a suitable container where the solvent can be removed by evaporation, e.g., first with a stream of dry, inert gas such as argon and then by high vacuum treatment.

According to the present invention, the immunogenic composition of the present invention can be used to immunize a vertebrate. The term "vertebrate" is intended to encompass a singular "vertebrate" as well as plural "vertebrates", and comprises mammalian and avian species, as well as fish. The method for immunizing a vertebrate includes administering to the vertebrate an immunogenic composition of the present invention in an amount sufficient to generate an immune response to the immunogen.

The immunogenic compositions of the present invention may be administered according to any of various methods known in the art. For example, U.S. Pat. No. 5,676,954 reports on the injection of genetic material, complexed with cationic lipid carriers, into mice. Also, U.S. Pat. Nos. 5,589, 466, 5,693,622, 5,580,859, 5,703,055, and PCT international patent application PCT/US94/06069 (WO 94/29469), the disclosures of which are incorporated herein by reference, provide methods for delivering DNA-cationic lipid complexes to mammals.

Specifically, the immunogenic compositions of the present invention may be administered to any tissue of a vertebrate, including, but not limited to, muscle, skin, brain, lung, liver, spleen, bone marrow, thymus, heart, lymph, blood, bone, cartilage, mucosal tissue, pancreas, kidney, gall bladder, stomach, intestine, testis, ovary, uterus, vaginal tissue, rectum, nervous system, eye, gland, tongue and connective tissue. Preferably, the compositions are administered to skeletal muscle. The immunogenic compositions of the invention may also be administered to a body cavity, including, but not limited to, the lung, mouth, nasal cavity, stomach, peritoneum, intestine, heart chamber, vein, artery, capillary, lymphatic, uterus, vagina, rectum, and ocular cavity.

Preferably, the immunogenic compositions of the present invention are administered by intramuscular (i.m.) or subcutaneous (s.c.) routes. Other suitable routes of administration include transdermal, intranasal, inhalation, intratracheal, transmucosal (i.e., across a mucous membrane), intra-cavity (e.g., oral, vaginal, or rectal), intraocular, vaginal, rectal, intraperitoneal, intraintestinal and intravenous (i.v.) administration.

Any mode of administration can be used so long as the administration results in desired immune response. Administration means of the present invention include, but not limited to, needle injection, catheter infusion, biolistic injectors, particle accelerators (i.e., "gene guns" or pneumatic "needleless" injectors—for example, Med-E-Jet (Vahlsing, H., et al., *J. Immunol. Methods* 171, 11-22 (1994)), Pigjet (Schrijver, R., et al., *Vaccine* 15, 1908-1916 (1997)), Biojector (Davis, H., et al., Vaccine 12, 1503-1509 (1994); Gramzinski, R., et al., *Mol. Med.* 4, 109-118 (1998)), AdvantaJet, Medijector, gelfoam sponge depots, other commercially available depot materials (e.g., hydrojels), osmotic pumps (e.g., Alza minipumps), oral or suppositorial solid (tablet or pill) pharmaceutical formulations, topical skin creams, and decanting, use of polynucleotide coated suture (Qin et al., *Life Sciences* 65, 2193-2203 (1999)) or topical applications during surgery. The preferred modes of administration are intramuscular needle-based injection and intranasal application as an aqueous solution.

Determining an effective amount of an immunogenic composition depends upon a number of factors including, for example, the chemical structure and biological activity of the substance, the age and weight of the subject, and the route of administration. The precise amount, number of doses, and timing of doses can be readily determined by those skilled in the art.

In certain embodiments, the immunogenic composition is administered as a pharmaceutical composition. Such a pharmaceutical composition can be formulated according to known methods, whereby the substance to be delivered is combined with a pharmaceutically acceptable carrier vehicle, Suitable vehicles and their preparation are described, for example, in *Remington's Pharmaceutical Sciences,* 16th Edition, A. Osol, ed., Mack Publishing Co., Easton, Pa. (1980), and *Remington's Pharmaceutical Sciences,* 19th Edition, A. R. Gennaro, ed., Mack Publishing Co., Easton, Pa. (1995). The pharmaceutical composition can be formulated as an emulsion, gel, solution, suspension, lyophilized form, or any other form known in the art. In addition, the pharmaceutical composition can also contain pharmaceutically acceptable additives including, for example, diluents, binders, stabilizers, and preservatives. Administration of pharmaceutically acceptable salts of the polynucleotide constructs described herein is preferred. Such salts can be prepared from pharmaceutically acceptable non-toxic bases including organic bases and inorganic bases. Salts derived from inorganic bases include sodium, potassium, lithium, ammonium, calcium, magnesium, and the like. Salts derived from pharmaceutically acceptable organic non-toxic bases include salts of primary, secondary, and tertiary amines, basic amino acids, and the like.

For aqueous pharmaceutical compositions used in vivo, use of sterile pyrogen-free water is preferred. Such formulations will contain an effective amount of the immunogenic composition together with a suitable amount of vehicle in order to prepare pharmaceutically acceptable compositions suitable for administration to a vertebrate.

The present invention also provides kits for use in delivering a polypeptide to a vertebrate. Each kit includes a container holding 1 ng to 30 mg of an immunoge-encoding polynucleotide which operably encodes an immunogen within vertebrate cells in vivo. Furthermore, each kit includes, in the same or in a different container, an adjuvant composition comprising GAP-DMORIE and a co-lipid. Any of components of the pharmaceutical kits can be provided in a single container or in multiple containers. Preferably, the kit includes from about 1 ng to about 30 mg of a immunogen-encoding polynucleotide, more preferably, the kit includes from about 100 ng to about 10 mg of a immunogen-encoding polynucleotide.

Any suitable container or containers may be used with pharmaceutical kits. Examples of containers include, but are not limited to, glass containers, plastic containers, or strips of plastic or paper.

Each of the pharmaceutical kits may further comprise an administration means. Means for administration include, but are not limited to syringes and needles, catheters, biolistic injectors, particle accelerators, i.e., "gene guns," pneumatic "needleless" injectors, gelfoam sponge depots, other commercially available depot materials, e.g., hydrojels, osmotic pumps, and decanting or topical applications during surgery. Each of the pharmaceutical kits may further comprise sutures, e.g., coated with the immunogenic composition (Qin et al., *Life Sciences* (1999) 65:2193-2203).

The kit can further comprise an instruction sheet for administration of the composition to a vertebrate. The polynucleotide components of the pharmaceutical composition are preferably provided as a liquid solution or they may be provided in lyophilized form as a dried powder or a cake. If the polynucleotide is provided in lyophilized form, the dried powder or cake may also include any salts, entry enhancing agents, transfection facilitating agents, and additives of the pharmaceutical composition in dried form. Such a kit may further comprise a container with an exact amount of sterile pyrogen-free water, for precise reconstitution of the lyophilized components of the pharmaceutical composition.

The container in which the pharmaceutical composition is packaged prior to use can comprise a hermetically sealed container enclosing an amount of the lyophilized formulation or a solution containing the formulation suitable for a pharmaceutically effective dose thereof, or multiples of an effective dose. The pharmaceutical composition is packaged in a sterile container, and the hermetically sealed container is designed to preserve sterility of the pharmaceutical formulation until use. Optionally, the container can be associated with administration means and/or instruction for use.

The following examples are included for purposes of illustration only and are not intended to limit the scope of the present invention, which is defined by the appended claims.

EXAMPLES

The following examples demonstrate the surprising finding that various GAP-DMORIE:co-lipid complexed with an antigen-encoding pDNA can enhance subsequent immune response compared to presently known nucleic acid immunization methods when administered into murine or rabbit tissues.

Materials and Methods

The following materials and methods apply generally to all the examples disclosed herein. Specific materials and methods are disclosed in each example, as necessary.

Reagents

Sterile USP water and saline solutions were purchased from Baxter (Deerfield, Ill.). All other chemicals and solvents were purchased either from Sigma Chem. Corp. (St. Louis, Mo.) or Gallade Chemical (Escondido, Calif.). Both the 1,2- dioleoyl-sn-glycero-3-phosphoethanolamine (DOPE) and 1,2-diphytanoyl-sn-glycero-3-phosphoethanolamine (DPyPE) were purchased as chloroform solutions from Avanti Polar Lipids, Inc. (Alabaster, Ala.).

Preparation of Adjuvant and Immunogenic Compositions (±)-N-(3-aminopropyl)-N,N-dimethyl-2,3-bis(syn-9-tetradeceneyloxy)-1-propanaminium bromide (GAP-DMORIE, also called VC 1052) was synthesized using the published procedure for preparing the analogue cytofectin GAP-DLRIE (Wheeler et al., *Proc. Natl. Acad. Sci.* 93, 11454-11459 (1996)). Specifically, substituting syn-9-tetradecenyl methane sulfonate for dodecenyl methane sulfonate in the initial bis-alkylation of 3-dimethylamino-1,2-propanediol yielded the desired dialkenyl amine. Quatranization with 3-bromopropylphthalimide, followed by deprotection of the protected primary amine with hydrazine and extractive purification and sub-micron filtration afforded pure GAP-DMORIE as judged by analytical thin layer chromatography. Product identity was confirmed using high resolution proton NMR and infrared (IR) spectroscopies.

Cytofectin:co-lipid mixtures were prepared using the rehydrated thin-film method. Briefly, dried films were prepared in 2 ml sterile glass vials by evaporating the chloroform under a stream of nitrogen, and placing the vials under vacuum overnight to remove solvent traces. Each vial contained 1.5 mmole each of a cytofectin and a co-lipid. Liposomes were prepared by adding 1 ml SWFI (sterile water for injection, VWR, Philadelphia, Pa.) per vial followed by continuous vortexing for 5 min on the highest setting of a Genie Vortex Mixer (Fisher Scientific, Pittsburgh, Pa.). The resulting liposome solution contained 1.5 mM cytofectin. Formulations were prepared at final pDNA (phosphate):cationic lipid molar ratios of 8:1, 4:1, and 2:1. The molar concentration of pDNA phosphate is calculated by dividing the pDNA concentration (in mg/ml) by 330, the average nucleotide molecular mass. Liposomes (in SWFI) and pDNA (in 2× vehicle) were prepared at twice the final concentration in the formulation. An equal volume of liposomes was added to pDNA using a syringe and a 26 or 28 gauge needle. Liposomes were added in a steady stream, followed by brief, gentle vortex to mix (a few seconds on setting #4 of a Genie vortex mixer).

All cytofectin/co-lipid formulations used in this study remained uniformly opaque for several hours after preparation at room temperature without any visible aggregation. Formulations were injected 20 min-1.5 hours after complexation. In a typical injection, where 5 µg of pDNA was formulated with a cytofectin at 4:1 pDNA:cytofectin molar ratio, each muscle received 2.4 µg cytofectin and 10 µg neutral co-lipid in 50 µl of vehicle. Even the highest pDNA+cytofecin:co-lipid dose tested in the mouse model (corresponding to 100 µg VR4700 plasmid+48 µg GAP-DMORIE+60 µg DPyPE per mouse) did not appear to produce discomfort or result in any adverse reactions when injected into mouse muscle.

Preparation of PDNAs

The VR4700 plasmid was prepared using standard techniques known in the art. Briefly, VR1255, an optimized plasmid encoding firefly luciferase (Hartikka, J., et al., *Human Gene Therapy* 7, 1205-1217 (1996)), had the coding sequence for influenza nuclear protein (NP) inserted in place of the luciferase coding sequence. The influenza nuclear protein sequence was derived from a plasmid termed nCMVint-tpa-PRNP (Vahlsing, L., et al., *J. Immunol. Methods* 174, 11-22 (1994)). More specifically, the VR4700 plasmid was created via the following procedure. The VR1255 plasmid was digested with Acc I+Bam HI, then the ends were blunted with Klenow, thus affording the desired vector fragment. The nuclear protein coding sequence was obtained by digesting nCMVintTPAPRNP with Ace I+Eco RI, and blunting the ends with Klenow. Both the vector fragment and the insert fragment were purified, then ligated with T4 DNA ligase. The ligation products were transformed in *E. coli* to kanamycin resistance, after which suitable plasmid bearing clones were identified based on restriction digest profiles. Standard cell culture techniques were used to expand a suitable clone, from which the plasmid was initially isolated and purified using well known, commercially available technology (Qiagen, Valencia, Calif.).

VR1412 LacZ plasmid was constructed by subcloning a cytoplasmic-targeted β-galactosidase gene into the VR1012 vector (Doh, S. G., et al., *Gene Therapy* 4(7), 268-263 (1997)). The VR1012 backbone vector contains the human cytomegalovirus (CMV) immediate early 1 promoter/enhancer, CMV intron A, bovine growth hormone terminator and kanamycin resistance gene (Hartikka, J., et al., *Human Gene Therapy* 7(10), 1205-17 (1996)).

VR5900 is a pDNA encoding hen egg lysozyme. For construction of this pDNA, gallus lysozyme cDNA was synthesized with overlapping oligonucleotides using Deep Vent DNA polymerase (NEB, Boston, Mass.). The nucleotide sequence was obtained from GENBank, accession V00428. The sequence was humanized with the OLIGO 5.0 program and the corresponding oligonucleotides purchased from Retrogen (San Diego, Calif.). The PCR product was cloned into pCRII Blunt Topo (Invitrogen, Carlsbad, Calif.), sequenced in its entirety and subcloned into VR1055. VR1055 is a Vical CMV promoter/enhancer-based expression vector that is identical to VR1012 except for the use of a minimal rabbit β-globin terminator in VR1055 (Hartikka, J., et al., *Human Gene Therapy* 7, 1205-17 (1996)). HEL expression was confirmed by western blot with a rabbit anti-egg white lysozyme (Biodesign, Kennebunk, Me.).

VR1904 is a pDNA encoding human factor IX. For construction, the factor IX cDNA insert from plasmid GT50 (kindly provided by Steven Josephs of Baxter Healthcare Corp., Round Lake, Ill.) was subcloned into the VR1012 vector.

VR1623 expresses a chimeric immunoglobulin with mouse variable regions fused to human constant regions. Human kappa and gamma (IgG1) constant regions were PCR amplified from human peripheral blood lymphocytes and cloned into VR1031, a bicistronic vector derived from VR1012 by insertion of a CITE sequence. This new construct was designated as VR1605. The variable region sequences from 38c13, a murine B-cell lymphoma (Bergman and Haimovich, 1977), were amplified by PCR from the plasmid pId (Tao and Levy, 1993, kindly provided by Dr. Ronald Levy, Stanford University Medical Center, CA) and cloned into VR1605 to make VR1623.

Bulk pDNA Preparation and Purification

Plasmid DNA was transformed into *Escherichia coli* DH10B or *Escherichia coli* DH5α competent cells and grown in Terrific Broth (Sambrook, J., et al., in *Molecular Cloning: A Laboratory Manual*, Cold Spring Harbor Laboratory Press, Cold Spring Harbor, N.Y., p. A.2 (1989)) supplemented with 50 mg/ml kanamycin in a 1 L shaker flask. Cells were harvested by centrifugation at the end of the exponential growth phase (approximately 16 hr), typically yielding 10 grams of biomass net weight per liter. Covalently closed circular pDNA was isolated by a modified lysis procedure (Horn, N. A., et al., *Human Gene Therapy* 6, 565-573 (1995)) followed by standard double CsCl-ethidium bromide gradient ultracentrifugation with an average yield of approximately 5 mg per liter. Plasmids were ethanol precipitated and resolubilized in saline at 4° C. and dialyzed against saline. Endotoxin content was determined by the *Limulus* Amebocyte Lysate assay (Associates of Cape Cod, Inc., Falmouth, Mass.). All plasmid preparations were free of detectable RNA. Endotoxin levels were less than 7.0 Endotoxin Units/mg of plasmid DNA. The spectrophotometric $A_{260}/A_{280}$ ratios were between 1.75 and 2.0. Plasmids were ethanol precipitated and resuspended in the injection vehicle at 4° C. until completely dissolved. DNA was stored at −20° C. until use.

Animal Immunizations

The quadriceps muscles of restrained awake mice (female 8-12 week old BALB/c mice from Harlan Sprague Dawley, Indianapolis, Ind.) were injected with pDNA in 50 μl of vehicle using a disposable insulin syringe and a 28 gauge ½ inch needle (Becton-Dickinson, Franklin Lakes, N.J., Cat. No. 329430) fitted with a plastic collar cut from a micropipette tip. The collar length was adjusted to limit the needle tip penetration to a distance of about 2 mm into the central part of the rectus femoris muscle. Injection fluids and syringes were equilibrated to room temperature and the injection of a single 50 μl volume was carried out in 1-2 seconds.

Ketamine/xylazine anesthetized female New Zealand White rabbits (5-6 months of age, approximately 3 kg) were injected in the quadriceps muscle with 150 μg pDNA in 300 μl PBS using a 22 gauge 1 inch needle. Before injections, the injection site was shaved and cleaned with alcohol. The needle-free injection device, Biojector®2000 (Bioject Inc., Portland, Oreg.), was tested in rabbits. The Biojector®2000 is a $CO_2$ powered jet injection system. In a pilot experiment, it was confirmed that the Biojector®2000 can deliver Indian ink solution through skin and into muscle tissue.

Animal care throughout the study was in compliance with the "Guide for the Use and Care of Laboratory Animals", Institute of Laboratory Animal Resources, Commission on Life Sciences, National Research Council, National Academy Press, Washington, D.C., 1996 as well as with Vical's Institutional Animal Care and Use Committee.

Anti-NP ELISA

Ninety-six well plates (Corning Incorporated, Cat. No. 3690, Corning, N.Y.) were coated with 71-125 ng/well of influenza A/PR/804 nucleoprotein (NP) purified from recombinant baculoviral extracts in 100 μl BBS (89 mM Boric Acid+90 mM NaCl+234 mM NaOH, pH 8.3). The plates were stored overnight at +4° C. and the wells washed twice with BBST (BBS supplemented with 0.05% Tween 20, vol/vol). The wells were then incubated for 90 minutes with BB (BBS supplemented with 5% nonfat milk, wt/vol) and washed twice with BBST again. Two-fold serial dilutions of mouse or rabbit serum in BB, starting at 1:20, were made in successive wells and the solutions were incubated for 2 hours at room temperature. Wells were then rinsed four times with BBST. Sera from mice hyperimmunized with VR4700 NP plasmid DNA were used as a positive control and pre-immune sera from mice and rabbits were used as negative controls.

To detect NP-specific antibodies, either alkaline phosphatase conjugated goat anti-mouse IgG-Fc (Jackson ImmunoResearch Laboratories, Cat. No. 115-055-008, West Grove, Pa.) or goat anti-rabbit IgG-Fc (Jackson ImmunoResearch Laboratories, Cat. No. 111-055-008, West Grove, Pa.) diluted 1:5000 in BBS was added at 50 μl/well and the plates were incubated at room temperature for 2 hours. After 4 washings in BBST, 50 μl of substrate (1 mg/ml p-nitrophenyl phosphate, Calbiochem Cat. No. 4876 in 50 mM sodium bicarbonate buffer, pH 9.8 and 1 mM $MgCl_2$) was incubated for 90 min at room temperature and absorbance readings were performed at 405 nm. The titer of the sera was determined by using the reciprocal of the last dilution still giving a signal two times above background. Background was established using pre-immune serum diluted 1:20.

Splenocyte $^{51}$Cr Release Assays

Single cell suspensions of splenocytes were pelleted and resuspended in RPMI 1640 medium containing L-glutamine and 25 mM HEPES and supplemented with penicillin (100 U/ml), streptomycin (100 μg/ml), 55 μM β-mercaptoethanol and 10% FBS. Unless otherwise noted, all tissue culture media and reagents were obtained from Gibco BRL Life Technologies (Rockville, Md.). Then, $2.5 \times 10^7$ splenocytes were cultured for 5 days in 25 $cm^2$ tissue culture flasks in a total of 10 ml of media with $NP_{147-155}$ peptide (H-2K$^d$ TYQRTRALV) (SEQ ID NO: 1) or β-gal$_{876-884}$ peptide (H-2L$^d$ TPHPARIGL) (SEQ ID NO: 2) at 1 μg/ml and recombinant murine IL-2 (Roche Molecular Bichemicals, Indianapolis, Ind.) at 0.5 U/ml.

For the CTL assay, P815 cells were labeled with 0.15 mCi $Na_2^{51}CrO_4$ (NEN Life Science Products, Boston, Mass.) in 30 μl saline at 37° C. for 35 minutes. Labeled cells were pulsed with 20 μg NP peptide or β-gal peptide (H-2L$^d$ TPH-PARIGL) (SEQ ID NO: 2) in 1 ml RPMI 1640 media at 37° C. for 40 minutes or were used unpulsed. Duplicate titrations of splenocytes were prepared by serially diluting the cells 1:3 in 96 well round bottom plates (ICN Biomedicals, Aurora, Ohio). Target cells were added at $1 \times 10^4$ cells/well in a final volume of 200 μl/well at the designated effector:target ratios (E:T). The plates were centrifuged and incubated for 4 hours at 37° C. with 5% $CO_2$. Counts per minute were determined for 100 μl of supernatant from each well. Specific lysis was calculated as % specific lysis=[(a−b)/(c−b)]100 where a is the average cpm released in the presence of effectors, b is the average cpm released from target cells incubated in media only and c is the cpm released from target cells in the presence of 1% Triton-X 100.

Example 1

GAP-DMORIE/co-lipid Enhances the Humoral Immune Response to pDNA-Encoded Influenza Nucleoprotein (NP) in Mice The present example demonstrates a quantitative comparison of the effects of the administration of various GAP-DMORIE:co-lipid complexes with pDNA versus pDNA alone in providing anti-NP antibody responses.

Transfection of muscles with pDNA encoding an immunogen elicits both humoral and cellular immune responses. To determine the extent of transfection augmentation in an assay evaluating humoral immune response, changes in anti-NP antibody levels subsequent to immunization with an immunogen-encoding pDNA alone, and the same pDNA complexed with various adjuvant compositions, were quantified. The general features of the immunization assay are essentially as described by Ulmer et al. (*Science*, 259, 1745-1749 (1993)) and uses standard ELISA technology to quantify antibody titers.

Mice were immunized using pDNA encoding influenza nuclear protein (NP), complexed with cytofectins formulated as a 1:1 (mol:mol) mixture with a co-lipid. The cytofectins were analyzed at a pDNA/cytofectin molar ratio of 4:1. Each animal in the test group (five animals per group) was injected with 5 μg pDNA in 50 μl physiological saline (0.9% NaCl weight/volume in water) per leg in the rectus femoris muscle (10 μg pDNA total per animal) alone or as a cytofectin:co-lipid complex. Injections were performed at day "0" and at 3 weeks.

Figure 4:
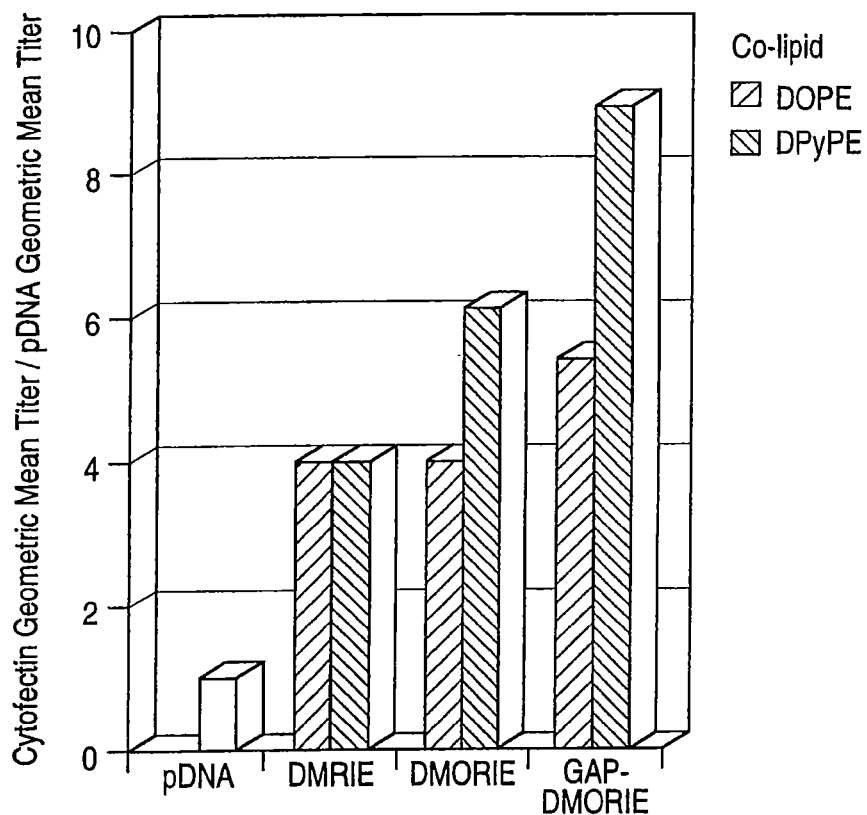
FIG. 4 is a bar graph illustrating the differential enhancement of anti-NP antibody responses to cytofectins by using DPyPE instead of DOPE as the co-lipid in the adjuvant composition. Mice were immunized and analyzed as described above in connection with FIG. 2.

Cytofectin:co-lipid immune response enhancement was analyzed based on the ratio of the geometric mean titer (GMT) from a cytofectin-augmented transfection group divided by the GMT from pDNA administration alone (see FIGS. 3 and 4). As shown in FIGS. 3 and 4, the preferred cytofectin GAP-DMORIE, when coupled with a co-lipid (especially DOPE or DPyPE), markedly enhances antibody responses to the encoded immunogen over both pDNA alone and pDNA complexed with other cytofectin:co-lipid combinations. Most surprisingly, the murine anti-NP antibody titers at six weeks post-i.m. injection of VR4700 (FIG. 4) complexed with GAP-DMORIE:DPyPE resulted in a 10-fold increase in geometric mean anti-NP titer.

Example 2

GAP-DMORIE/DPyPE Enhances the Humoral Immune Response to pDNA-Encoded Influenza Nucleoprotein (NP) in Mice The purpose of the present example is to demonstrate the ability of the preferred cytofectin:co-lipid, GAP-DMORIE/DPyPE, to enhance the humoral immune response to pDNA-encoded NP antigen. The most preferred cytofectin:co-lipid mixture is GAP-DMORIE/DPyPE at a 1:1 molar ratio. Rather than employing the more cumbersome formal chemical nomenclature and stipulating the specific molar ratio for the mixture, this novel formulation has been named "Vaxfectin."

β-Galactosidase Assay

The muscle tissues were harvested, pulverized and extracted as previously described (Manthorpe, M., et al, *Gene Quantification*. Boston, Birkhauser 343-368 (1998)). The level of β-galactosidase expression in muscle extracts was quantified using a chemiluminescent assay according to the manufacturer's instructions (Boehringer Mannheim, Cat. No. 1758241, Indianapolis, Ind.). A standard curve, prepared in pooled extract from uninjected muscles, was included on each plate using the β-galactosidase enzyme standard included in the kit.

Quantitation of Anti-NP Specific Antibody Secreting Cells by ELISPOT Assay

Anti-NP specific antibody secreting cells were quantified by the ELISPOT method using a previously described protocol (Slifka, M. K., et al, *J. Virol.* 69(3), 1895-1902 (1995)). Cells obtained from bone marrow (femur and tibia) were treated with 0.83% $NH_4Cl$ to lyse red blood cells. Cells were then resuspended in RPMI 1640 medium containing 5% fetal calf serum (Hyclone, Logan, Utah), L-glutamine, HEPES, penicillin and streptomycin (LTI, Bethesda, Md.). Nitrocellulose-bottom 96-well Multiscreen filtration plates (Millipore Corporation, San Francisco, Calif.) were coated with 100 piper well of 5 µg/ml of NP antigen (influenza nucleoprotein strain A/PR/8/34) in PBS and incubated overnight at 4° C. Plates were blocked with RPMI 1640 containing 5% FBS for 2 h at room temperature. Blocking medium was replaced with 100 µl/well of blocking medium containing bone marrow cell suspension obtained from mice immunized with pDNA encoding influenza NP (with or without Vaxfectin), starting at $10^6$ cells, then diluted threefold row-wise down the plate. Control wells contained cells obtained from naïve mice diluted as above (earlier controls included an irrelevant antigen). Plates were incubated for 5 h at 37° C. in a 7% $CO_2$ humidified incubator. The plates were washed six times and incubated overnight at 4° C. with 100 µl per well of biotinylated horse anti-mouse IgG (H+L, 1/1000 dilution, Vector Laboratories, Burlingame, Calif.) in PBS-T containing 1% FBS. Plates were further incubated for 1 h at room temperature with 100 µl/well of 5 µg/ml of horseradish peroxidase-conjugated avidin D (Vector Laboratories, Burlingame, Calif.). Antibody secreting cells were detected by adding 100 µl per well of substrate (3-amino-9-ethylcarbazole and $H_2O_2$) to the plates for 3-5 minutes. The reaction was terminated by washing profusely with tap water. Spots were counted under a dissecting microscope. Anti-NP specific antibody secreting cells were represented as number of spots per $10^6$ bone marrow cells.

Statistical Evaluations

All statistical comparisons were performed using the nonparametric Mann-Whitney rank sum test (SigmaStat version 2.03, Jandel Scientific Software, San Rafael, Calif.). Differences were considered statistically significant when the p value was less than 0.05.

pDNA/Vaxfectin Dose Response

Figure 5:
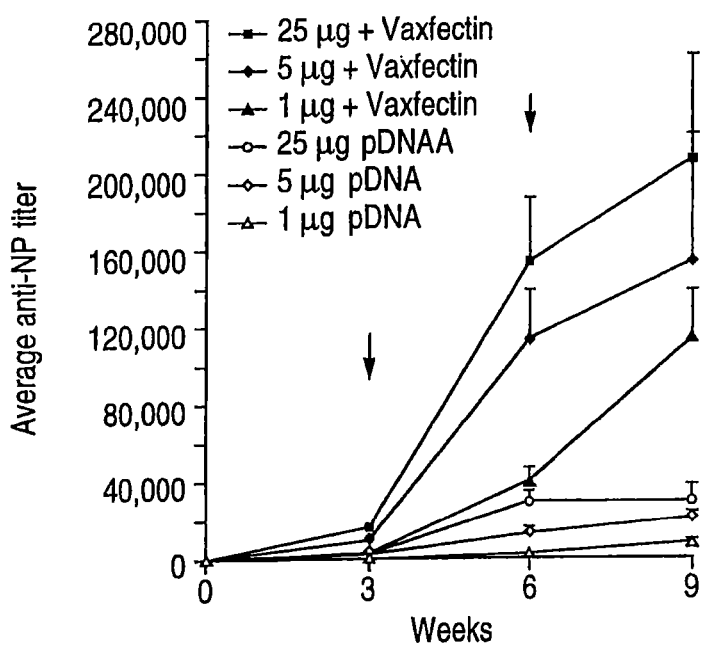
FIG. 5 illustrates pDNA-Vaxfectin vaccination dose response and time course. BALB/c mice (8-10 weeks old) received bilateral intramuscular injections of 1 μg, 5 μg or 25 μg naked VR4700 plasmid DNA encoding influenza nuclear protein (NP) in 50 μl PBS per muscle (thus, 2 μg, 10 μg or 50 μg total pDNA per time point). A second set of mice received the same pDNA doses formulated with Vaxfectin using a constant pDNA:cationic lipid molar ratio of 4:1. Boost injections were given on days 21 and 42 (arrows). Anti-NP titers were determined from serum samples at 3, 6 and 9 weeks. The lines represent average anti-NP antibody titers+S.E.M. (n=5 mice per group).

To compare the effects of increasing pDNA dose, and the effect of boost injections, mice were given bilateral i.m. injections of 1 µg, 5 µg or 25 µg of naked VR4700 plasmid per muscle (thus affording a total pDNA dose of 2, 10 and 50 µg per animal, respectively) at three-week intervals. The results are shown in FIG. 5. Higher anti-NP titers were reached when more naked pDNA was injected per muscle, and titers increased after the first and the second boost injections. However, no further increase in anti-NP titers was observed with any of the pDNA doses when a third boost injection was given at 9 weeks (data not shown), suggesting that plateau antibody titer levels had been reached with naked pDNA.

A second set of mice received equivalent pDNA doses formulated with Vaxfectin. The results are shown in FIG. 5. Here, a 7- to 20-fold increase in antibody titers with all three pDNA doses was observed. The highest average anti-NP titers per group in this experiment (204,800±56,087, n=5 mice) were measured at 9 weeks with 25 µg pDNA dose formulated with Vaxfectin. As was seen with naked pDNA injections, no further increase in anti-NP titers was observed with any of the Vaxfectin groups when a third boost injection was given at 9 weeks (data not shown). Thus, Vaxfectin enhanced antibody titers to levels that could not be reached with naked pDNA alone, either by increasing the pDNA dose or the number of injections. The most striking finding was that as little as 1 µg of pDNA per muscle formulated with Vaxfectin resulted in up to 5-fold higher anti-NP titer than that obtained with 25 µg naked VR4700 alone.

A separate experiment was done to address whether multiple bilateral injections are required to obtain Vaxfectin-mediated enhancement in humoral immune response. The results are shown in Table 1. Formulating 5 µg VR4700 pDNA with Vaxfectin produced a significant 6-fold increase in anti-NP titers 20 days after a single unilateral i.m. injection in mice, indicating that Vaxfectin can enhance antibody response after a single dose.

TABLE 1

Antibody titers in mouse serum after a unilateral i.m. injection of pDNA coding for influenza nuclear protein (NP) protein[a].

| | Average anti-NP titers | | |
|---|---|---|---|
| | pDNA | Vaxfectin | Fold Increase |
| Day 20 | 710 ± 162 | 4,573 ± 1,243[b] | 6 x |
| Day 42 | 5,387 ± 767 | 35,200 ± 6,096[b] | 7 x |

[a]Mice received a single injection of 5 µg naked VR4700 plasmid in 50 µl of 150 mM NaP in the right quadriceps muscle. A second group of mice received 5 µg VR4700 formulated with Vaxfectin at a pDNA:cationic lipid molar ratio of 4:1. On day 21, mice were given a single boost injection in the same muscle. Total NP-specific IgG antibody titers were determined from serum samples on day 20 and 42 (average ± S.E.M., n = 15 mice).
[b]Significantly different from naked pDNA control value (p < 0.01, Mann-Whitney rank sum test).

Formulation Optimization

Figure 6A:
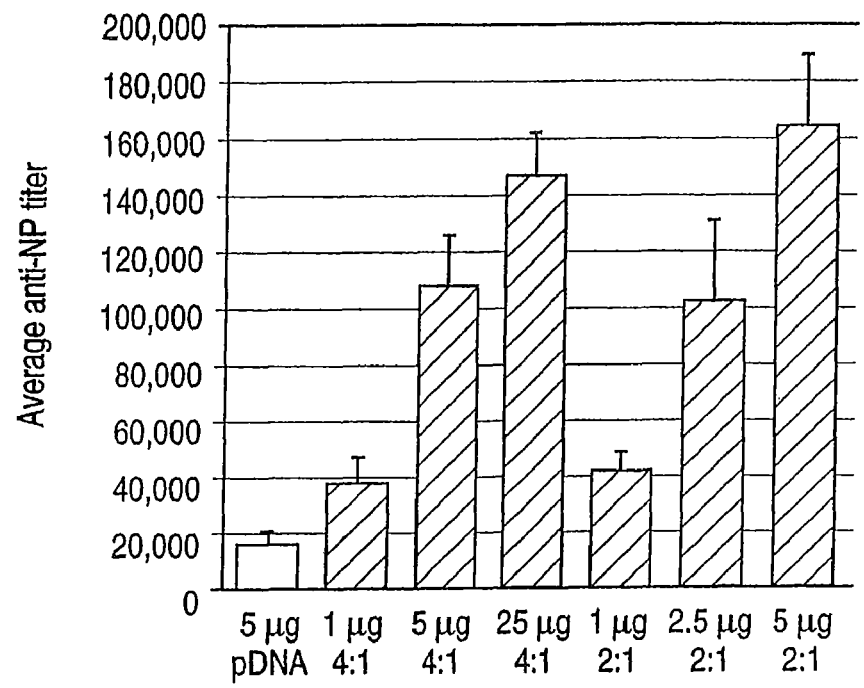
FIGS. 6A and 6B illustrate Vaxfectin formulation optimization. Control mice received bilateral intramuscular injections of 5 μg naked VR4700 plasmid DNA encoding influenza nuclear protein (NP) in 50 μl PBS per muscle (white bars). The test groups received an equivalent pDNA dose formulated with Vaxfectin at the indicated pDNA:cationic lipid molar ratios (black bars). Boost injections were identical to the initial injections, and were given on day 21. Total NP-specific IgG antibody titers were determined from serum samples on day 42 (3 weeks after the boost). The bars represent average anti-NP titers from two separate experiments (n=5-15 mice per group).
Figure 6B:
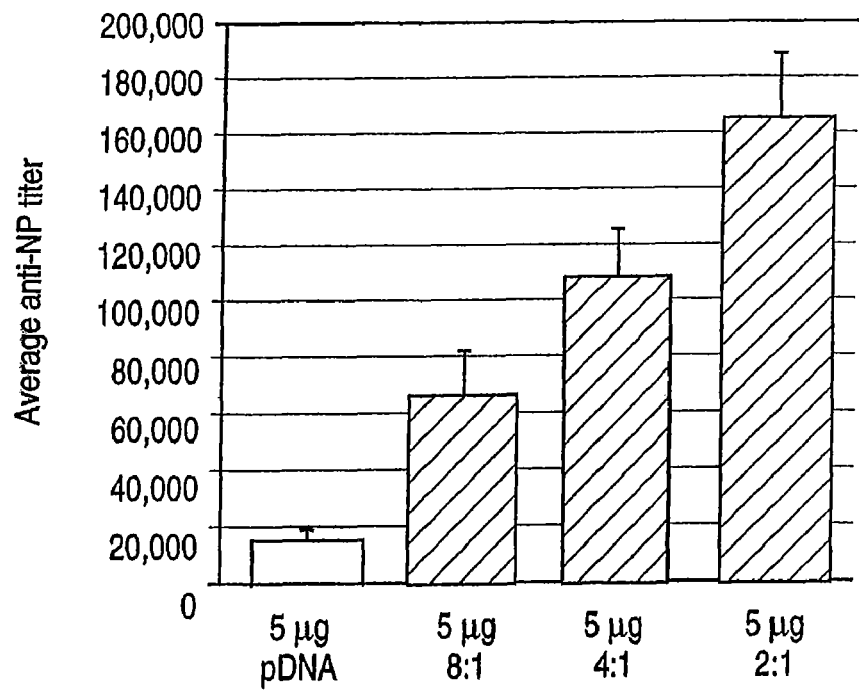

Different pDNA:cationic lipid ratios were tested in the murine immunization model to optimize Vaxfectin formulations. The results, shown in FIG. 6, indicate that injecting more pDNA-Vaxfectin complex (thus, increasing both the amount of plasmid and the amount of Vaxfectin simultaneously) increased antibody titers in a dose dependent manner. This trend was observed for both the 2:1 and 4:1 pDNA:cationic lipid molar ratios. When the same 5 µg pDNA dose was injected with increasing amount of Vaxfectin (thus decreasing the pDNA:cationic lipid molar ratio), antibody titers again increased in a Vaxfectin dose dependent manner (FIG. 6B). Higher pDNA doses were also examined, but injecting 50 µg pDNA per limb formulated with Vaxfectin at 4:1 pDNA:cationic lipid molar ratio did not produce any further increase in anti-NP titers, compared to 25 µg pDNA formulated with Vaxfectin at the same 4:1 ratio (data not shown).

Duration of Enhanced Humoral Response

Figure 7A:
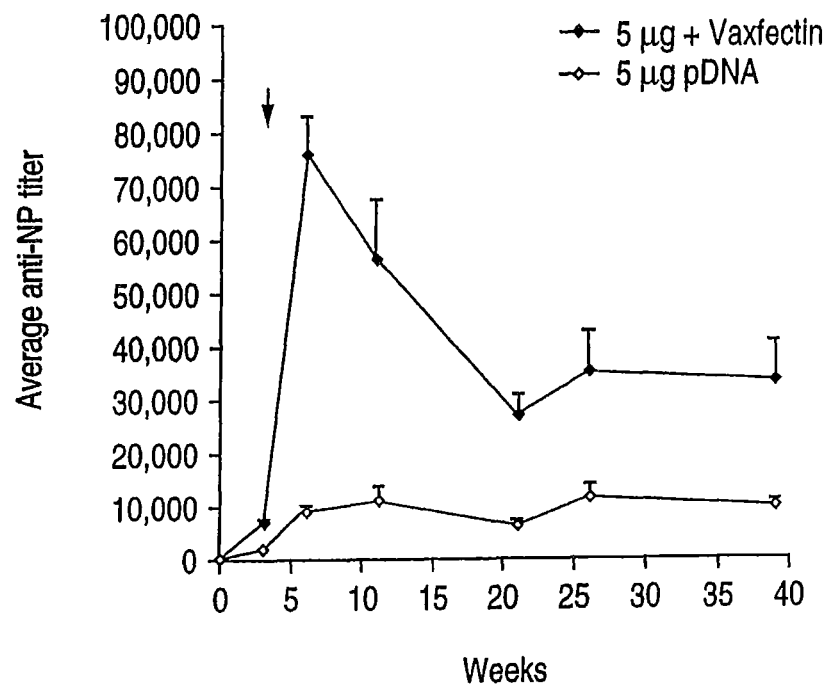
FIGS. 7A and 7B illustrate the duration of elevated antibody titers induced by Vaxfectin. Mice received bilateral intramuscular injections of either 5 μg naked VR4700 plasmid DNA encoding influenza nuclear protein (NP) in 50 μl PBS per muscle, or the same amount of pDNA formulated with Vaxfectin at a pDNA:cationic lipid molar ratio of 4:1. Identical boost injections were given either on day 21 (A), or on day 21 and again at 3 months (13) (arrows). Total NP-specific IgG antibody titers were determined from serum samples at various time points. The lines represent average anti-NP titers+S.E.M. (n=4-10 mice per time point).

To investigate the duration of the Vaxfectin-enhanced humoral response, NP specific antibody titers were followed for nine months after initial injection in the murine vaccination model. The results are shown in FIG. 7A. Three weeks after the boost injection given on day 21, anti-NP titers in the Vaxfectin group were 9-fold higher than in the naked pDNA control group. During the subsequent weeks, antibody titers in the Vaxfectin group gradually declined but remained significantly higher than in the controls throughout the course of the experiment. Forty weeks after the start of the experiment, anti-NP titers in Vaxfectin group were still 4-fold higher than in the naked pDNA group.

Figure 7B:
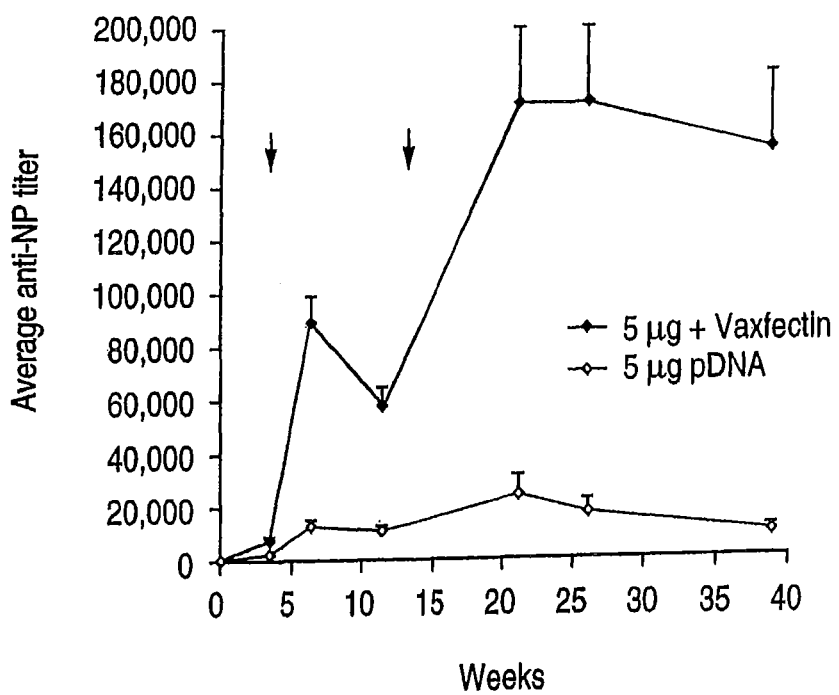

In a parallel experiment, another set of mice received a boost injection on week 3, and a second identical boost at 3 months. The results are shown in FIG. 7B. The second boost injection increased antibody titers in both groups by 2- to 3-fold. However, anti-NP titers in the Vaxfectin group appeared to remain at these elevated levels for several months, whereas the naked pDNA group yielded titers comparable to those after a single boost at the end of the experiment. Consequently, nine months after the start of the experiment, anti-NP titers in Vaxfectin group were 17-fold higher than in the pDNA control group.

Vaxfectin Maintains a Strong Ctl Response

Figure 8A:
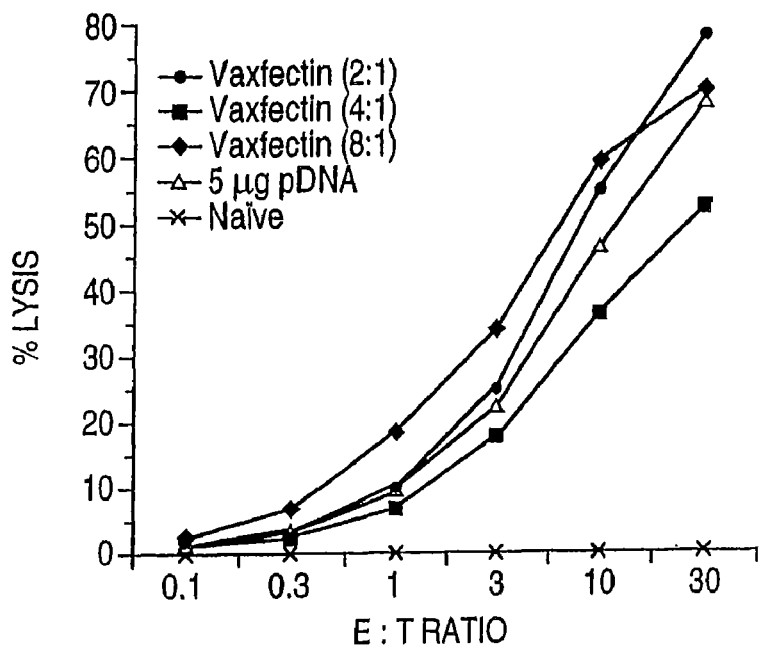
FIGS. 8A, 8B, and 8C illustrate that pDNA formulated with Vaxfectin induces CTL responses that are as robust as those induced with naked pDNA. (A) Mice received bilateral intramuscular injections of 5 µg VR4700 plasmid DNA encoding influenza nuclear protein (NP) in 50 µl PBS per muscle on day 0, 21, 42 and 63. A second set of mice received the same pDNA dose formulated with Vaxfectin at the indicated pDNA:cationic lipid molar ratios. (B) Mice received bilateral intramuscular injections of 1 or 25 µg VR4700 plasmid in 50 µl PBS per muscle on day 0, 21, 42 and 63. A second set of mice received the same pDNA doses formulated with Vaxfectin at a pDNA:cationic lipid molar ratio of 4:1. (C) Mice received bilateral intramuscular injections of 5 µg VR4700 plasmid in 50 µl 150 mM NaP per muscle on day 0 and 21. A second set of mice received the same pDNA dose formulated with Vaxfectin at a pDNA:cationic lipid molar ratio of 4:1. All CTL assays were performed 4-4.5 months after the first injection. The lines represent average specific lysis (n=4-5 mice per group).
Figure 8B:
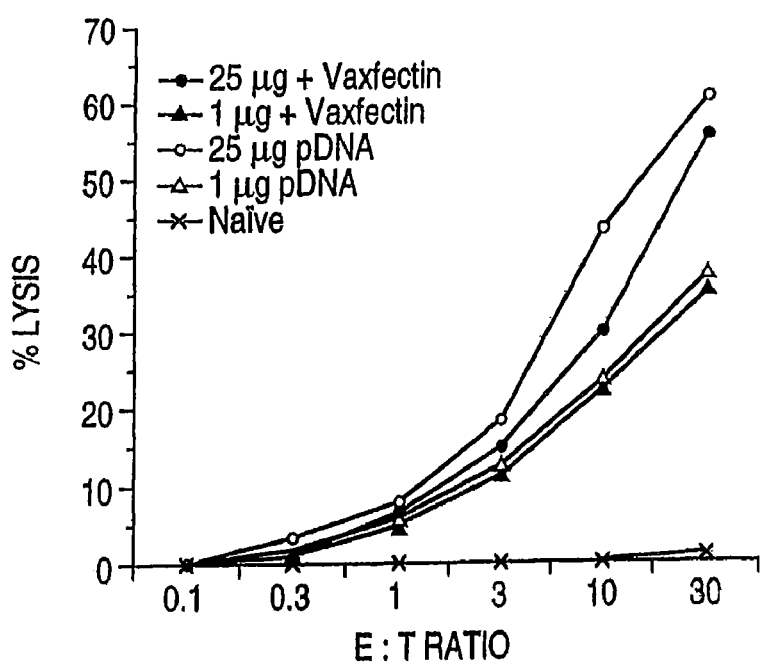
Figure 8C:
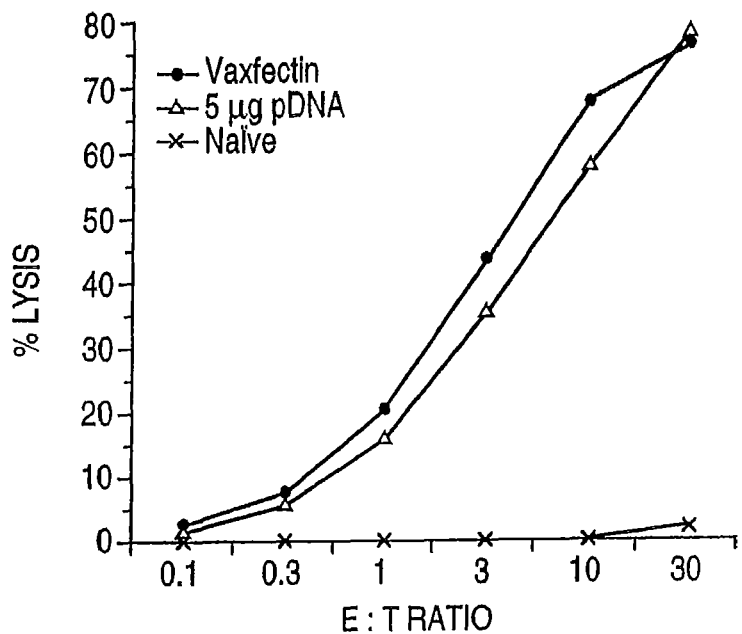

It would be highly desirable that an adjuvant used in combination with pDNA vaccines to enhance humoral immune response would not at the same time diminish cell-mediated immunity. To evaluate this, CTL assays were performed after mice had been injected with various doses of pDNA with or without Vaxfectin. The results are shown in FIG. 8. Vaxfectin did not have a significant effect on CTL response when formulated at different pDNA and cationic lipid ratios (FIG. 8A), after a single boost (FIG. 8C) or multiple boost injections (FIGS. 8A and 8B), or when delivered in PBS (FIG. 8A) or 150 mM NaP vehicle (FIG. 8C). Injecting 25 µg of naked pDNA per muscle appeared to result in stronger CTL responses than 1 µg pDNA dose. Again, Vaxfectin did not have a significant effect on CTL response with either pDNA dose (FIG. 8B). Taken together, these results show that Vaxfectin could be used to enhance humoral immune response with pDNA vaccines while maintaining the strong CTL response characteristic of pDNA immunization.

Vaxfectin does not Increase Muscle Transfection

Figure 9:
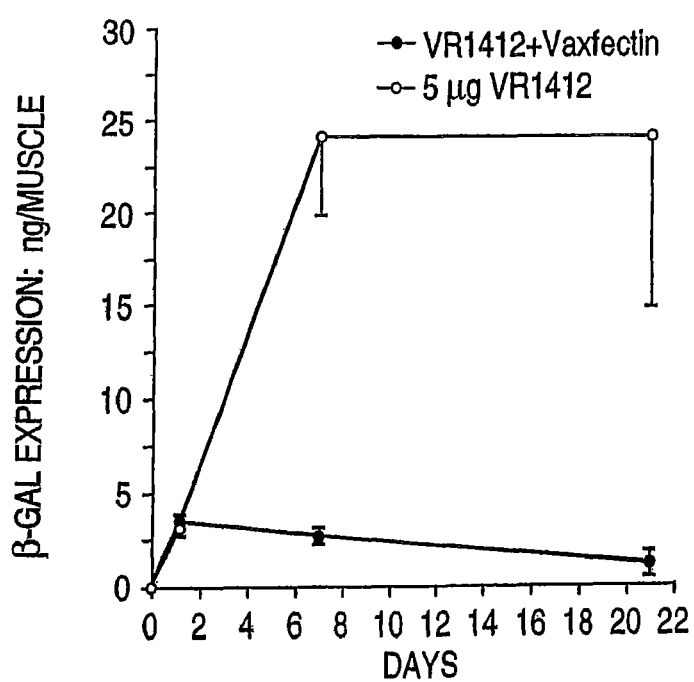
FIG. 9 illustrates the effect of Vaxfectin on β-galactosidase (β-Gal) expression in muscle. Mice received intramuscular injections of 5 µg naked VR1412 plasmid encoding β-galactosidase. A second group of mice was injected with 5 µg VR1412 formulated with Vaxfectin at a pDNA:cationic lipid molar ratio of 4:1. At the indicated time points, quadriceps muscles were harvested and assayed for β-Gal activity. The lines represent average reporter gene expression per muscle ±S.E.M. (n=10-20 muscles per group).

To elucidate the mechanism by which Vaxfectin enhances antibody responses, the effect of Vaxfectin on muscle expression in vivo was studied. In these experiments, pDNA (VR1412) encoding β-galactosidase was injected either alone or formulated with Vaxfectin and individual muscles were periodically assayed for reporter gene expression. The results are shown in FIG. 9. One day after injections, β-galactosidase expression in both groups was the same, indicating that Vaxfectin did not affect the initial transfection of muscle with pDNA. Between day 1 and 7, muscle expression in the naked pDNA group increased 7-fold. In contrast, expression in the Vaxfectin group decreased by 25% during the same time period. Between day 7 and 21, reporter gene levels remained the same in the naked pDNA group, whereas β-galactosidase expression in muscle continued to decline in the Vaxfectin group and was more than 20-fold lower than in the pDNA control group at day 21. Thus, at later time points, transgene expression in muscle was markedly reduced in the Vaxfectin group, whereas antibody levels were higher. This lack of correlation between muscle expression and antibody titers indicates that Vaxfectin mediated enhancement in antibody response cannot be explained by facilitated transfection of myofibers and/or increased synthesis of the antigen in muscle tissue.

The mechanism by which Vaxfectin enhances the antigen-specific antibody response is unclear. It is possible that Vaxfectin delivers the pDNA to multiple cell types within muscle tissue, including antigen-presenting cells, whereas needle injection of pDNA without Vaxfectin might principally transfect muscle fibers. Alternatively, the pDNA-lipid complex may be better able to exit the muscle and transduce distal tissue, including cells in the regional draining lymph nodes. Vaxfectin could protect the plasmid against nucleases, enabling the pDNA-lipid complex to reach tissues distant from the injection site. Vaxfectin may also induce inflammation, resulting in the damage of many transduced muscle fibers and thereby releasing more soluble antigen soon after injection. A decrease in antigen production in the following days may select for higher affinity antigen specific B cells by limiting antigen, resulting in an increase in antibody titers.

Vaxfectin Increases the Number of Antigen-specific Plasma Cells in Bone Marrow

Elevated anti-NP titers in Vaxfectin treated animals were maintained for several months after the boost injection (FIG. 7). Since long-lived plasma cells in bone marrow have been shown to be the major mechanism for maintaining persistent antibody production after viral infection (Slifka, M. K., et al, J. Virol. 69(3), 1895-1902 (1995), Slifka, M. K., et al, Curr. Opin. Immunol 10(3), 252-258 (1998)) the number of anti-NP antibody secreting cells from bone marrow was quantified using an ELISPOT assay. The results showed that Vaxfectin produced a statistically significant 3- to 5-fold increase in the number of NP specific plasma cells in bone marrow. Furthermore, antibody titers in individual mice roughly correlated with the number of anti-NP antibody secreting cells in bone marrow, both in the naked pDNA and in the Vaxfectin groups (Table 2).

TABLE 2

Quantitation of anti-NP antibody secreting cells in bone marrow by ELISPOT assay

| | | PDNA | | | Vaxfectin | |
|---|---|---|---|---|---|---|
| | Mouse | Anti-NP Titer | SFC per $10^6$ cells | Mouse | Anti-NP titer | SFC per $10^6$ cells |
| Experiment 1[a] | 1 | 3,200 | 1.8 | 1 | 51,200 | 17.3 |
| | 2 | 12,800 | 5.0 | 2 | 102,400 | 11.8 |
| | 3 | 25,600 | 8.3 | 3 | 102,400 | 29.8 |
| | 4 | 51,200 | 13.7 | 4 | 204,800 | 21.2 |
| | | | | 5 | 204,800 | 34.8 |
| | Average | 23,200 | 7.2 | Average | 133,120 | 23.0[b] |
| Experiment 2[c] | 1 | 12,800 | 11.0 | 1 | 51,200 | 39.5 |
| | 2 | 12,800 | 15.0 | 2 | 102,400 | 35.0 |
| | 3 | 25,600 | 12.5 | 3 | 204,800 | 85.2 |
| | 4 | 51,200 | 21.3 | 4 | 204,800 | 132.8 |
| | Average | 25,600 | 14.9 | Average | 140,800 | 73.1[d] |

[a]Mice received bilateral intramuscular injections of 5 µg VR4700 pDNA in 50 µl PBS, either alone or formulated with Vaxfectin at 4:1 pDNA:cationic lipid molar ratio. Identical boost injections were given at three weeks and at three months. Mice were sacrificed four months after the start of the experiment (one month after the second boost injection). Antibody titers were measured from terminal bleeds and the number of anti-NP specific spot forming cells (SFC) per $10^6$ bone marrow cells were quantified.
[b]Significantly different from pDNA control value (p = 0.032, Mann-Whitney rank sum test).
[c]Mice received bilateral intramuscular injections of 5 µg VR4700 pDNA in 50 µl PBS, either alone or formulated with Vaxfectin at 4:1 pDNA:cationic lipid molar ratio. Identical boost injections were given at three weeks and at nine months. Mice were sacrificed eleven months after the start of the experiment (two months after the second boost injection). Antibody titers were measured from terminal bleeds and anti-NP secreting cells were quantified from bone marrow.
[d]Significantly different from pDNA control value (p = 0.029, Mann-Whitney rank sum test).

The data from the ELISPOT assays indicate that the use of Vaxfectin increases the number of antigen specific plasma cells in the bone marrow. This increase in plasma cells may be due to the adjuvant properties of the pDNA-lipid complexes. Injection of blank pDNA complexed with a cationic lipid into the peritoneum of murine ovarian tumor bearing C3H/HeN mice induces the production of IL-6, IFN-γ, and TNF-α (Horton, H. M., et al, *J. Immunol.* 163(12), 6378-6385 (1999)). These cytokines were not induced in mice treated with pDNA or lipid only, suggesting that the pDNA-lipid complexes are immunostimulatory in vivo. The immunostimulatory properties of pDNA-lipid complexes were also reported for experiments in which mice were injected intravenously with pDNA complexed with cationic lipid (Dow, S. W., et al, *J. Immunol.* 163(3), 1552-1561 (1999)). As for intraperitoneal and intravenous injection of pDNA-lipid complexes, intramuscular injection of pDNA-Vaxfectin may also induce cytokines, including IL-6, a cytokine that promotes the differentiation of activated B cells to plasma cells. Thus, the pDNA-Vaxfectin complexes may indirectly enhance antibody titers by increasing the number of antibody producing B cells.

It is also possible that components of Vaxfectin might mimic naturally occurring mitogens that can directly stimulate polyclonal expansion of B cells. This could enhance the specific immune response against the transgene expressed by the muscle cells by increasing the number of responding B cells. Thus, increased transfection of APCs or delivery of pDNA to the draining lymph nodes with transfection of cells in the lymph nodes, muscle damage resulting in increased availability of soluble antigen and the immunostimulatory properties of the pDNA-Vaxfectin complexes could each contribute to the adjuvant effect of Vaxfectin.

Example 3

Vaxfectin Enhances Antibody Titers in Rabbits

The purpose of the present example is to demonstrate the adjuvant effect of GAP-DMORIE:co-lipids (e.g., Vaxfectin) in rabbits when formulated in polynucleotide-based vaccines.

Female New Zealand white rabbits (5-6 months old) were anesthetized, then injected in a hind leg with 300 µl of a PBS solution containing either 150 µg of VR4700 plasmid DNA or a PBS solution containing a complex of 150 µg VR4700 plasmid with GAP-DMORIE:DPyPE (1:1) prepared at a 4:1 mol:mol pDNA:GAP-DMORIE ratio. Each rabbit received a single injection using a sterile disposable, plastic insulin syringe and 22 gauge 1 inch needle at day zero, plus an identical "boost" injection in the opposite hind leg at 6 weeks. The animals were bled through an ear vein prior to immunization, and at weeks 3, 6, 7, 9, and 13. The six-week bleed was performed the same day, but before boost injection was given.

Figure 10:
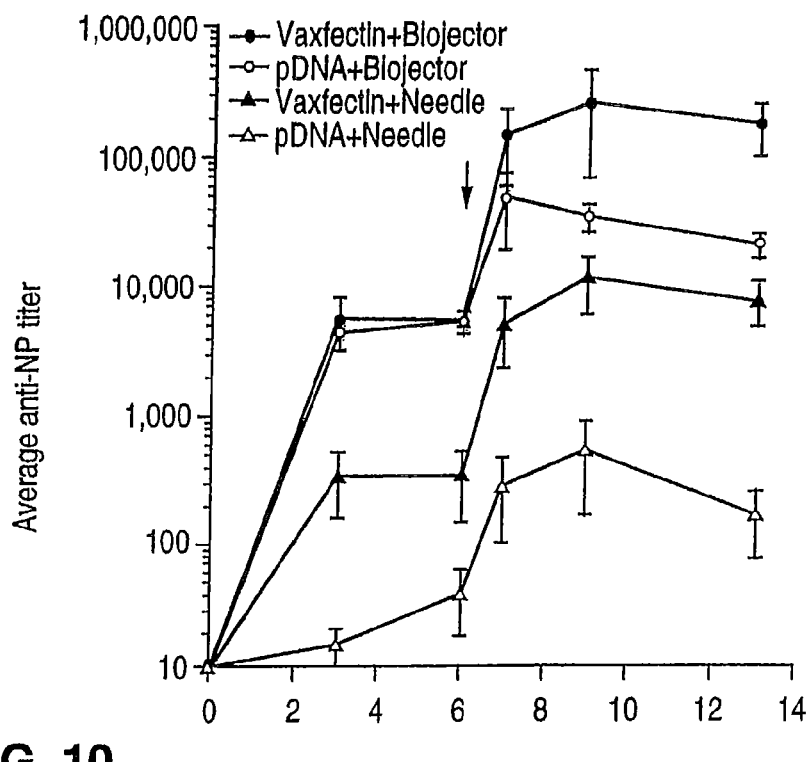
FIG. 10 illustrates that Vaxfectin enhances humoral immune response in rabbits, Total IgG antibody titers in rabbit serum after i.m. injection of VR4700 plasmid DNA encoding influenza nuclear protein (NP) are shown. New Zealand White rabbits (5-6 months old) received a single unilateral injection of either 150 µg VR4700 plasmid alone or formulated with Vaxfectin (pDNA:cationic lipid=4:1 molar ratio) in 300 µl PBS. In one group of animals (triangles), both pDNA and pDNA-Vaxfectin were injected using needle and syringe. In another group of rabbits (circles), pDNA and pDNA-Vaxfectin were injected using a Biojector needle-free injection device. On day 42 (arrow), rabbits were given an identical boost injection in the contralateral quadriceps muscle. Anti-NP titers were determined from serum samples collected prior to immunization, and at weeks 3, 6, 7, 9, and 13. The lines represent average anti-NP titers+S.E.M. (n=4 rabbits per group).
Figure 11A:
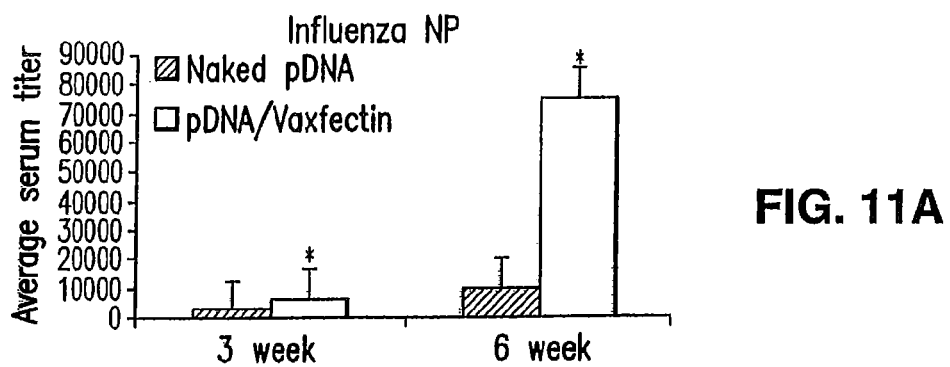
FIGS. 11A, 11B, 11C, 11D, and 11E illustrate that Vaxfectin enhances antigen specific serum antibody responses to 5 different pDNA encoded model antigens. BALB/c mice were immunized with injections of 5 µg pDNA+/−Vaxfectin into each rectus femoris muscle at 0 and 3 weeks. Data shown are the mean antigen specific IgG titers (+/−SEM) for sera collected 1 day prior to the boost at 3 weeks and at 6 weeks. (n=20 for all groups, except for NP where n=29 for Naked NP pDNA; n=30 for NP pDNA/Vaxfectin and mouse Id where n=19 for naked pDNA.) A) Anti-influenza NP IgG titers; B) Anti-influenza HEL IgG titers; C) Anti-β-gal IgG titers; D) Anti-Mouse Id IgG titers; E) Anti-Factor IX IgG titers. *Statistically significant difference from titers obtained with naked pDNA, p≦0.05.
Figure 11B:
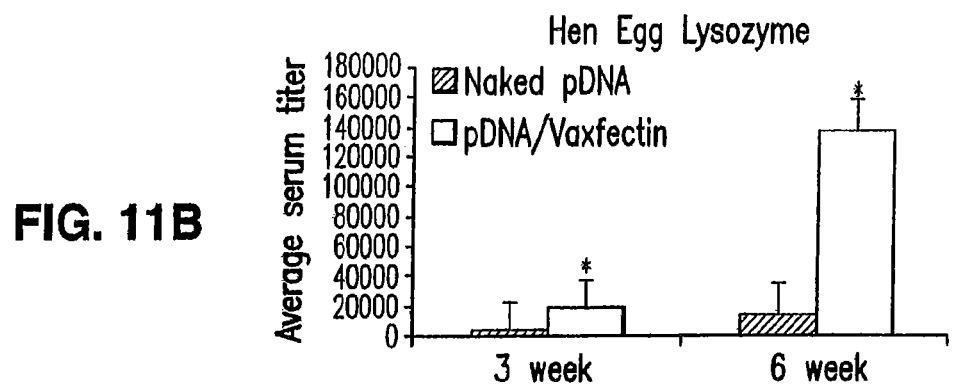
Figure 11C:
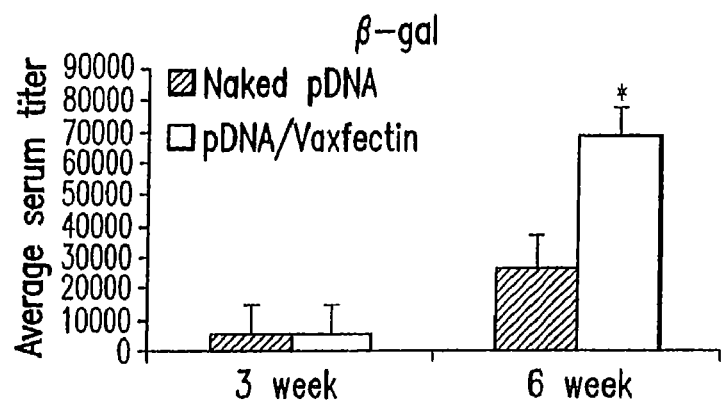
Figure 11D:
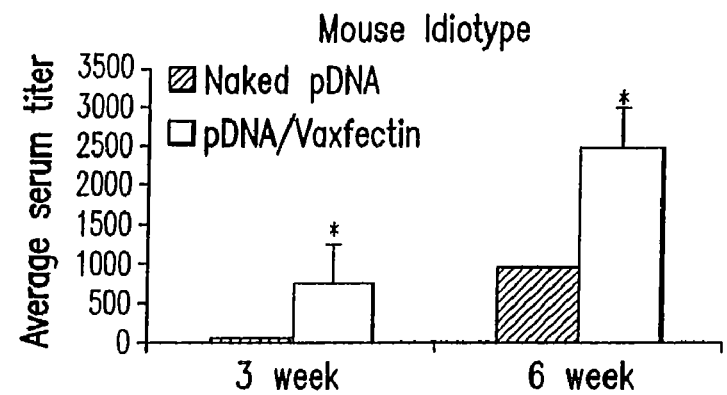
Figure 11E:
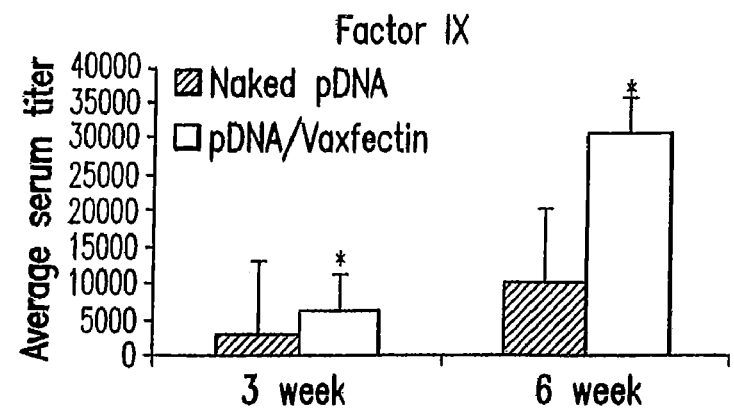

Using a single unilateral i.m. injection performed with needle and syringe, Vaxfectin produced a robust 20-fold increase in antibody titers at three weeks compared to injection of naked pDNA. The results are shown in FIG. 10. After a boost injection given at 6 weeks, anti-NP titers in both groups increased approximately by an order of magnitude, with antibody titers in the Vaxfectin group remaining 20- to 50-fold higher than in the naked pDNA group throughout the course of the experiment. When rabbits were immunized with the Biojector®2000 device, Vaxfectin did not appear to enhance antibody response after a single unilateral injection. After a boost injection was given at 6 weeks, anti-NP titers in the Biojector Vaxfectin group were up to 8-fold higher than in the corresponding naked pDNA group.

Example 4

Vaxfectin Enhances Antibody Production and Promotes TH1 Type Immune Response to Various Plasmid DNA-Encoded Antigens The purpose of the present example is to demonstrate the adjuvant effect of GAP-DMORIE:co-lipid (e.g., Vaxfectin) when formulated with various model antigens, and to further characterize the immune responses to pDNA formulations containing GAP-DMORIE:co-lipid.

Immunization and Serum Collection

Restrained, awake mice received 5 μg of pDNA encoding A/PR/8/34 NP (VR4700), hen egg lysozyme (HEL, VR5900), E. coli Lac Z (β-gal, VR1412), mouse Id/human Fc (immunoglobulin variable regions from 38C13, a murine lymphoma cell line fused to a human IgG1 constant region, VR1623), or human factor IX (VR1904) prepared in PBS with and without Vaxfectin (50 μl) and injected into the rectus femoris of 8-10 week old female mice. Mice were boosted at 3 weeks with the same dose and formulation. Mice were bled from the ophthalmic venous plexus prior to the first injection, 1 day prior to the boost, and at 6 weeks following the first injection.

IgG Antibody ELISAs

Antibody titers were determined by coating 96 well, ½ area flat well microtiter plates (Corning/Costar, Inc., Corning, N.Y.) with 0.035 μg influenza nucleoprotein (purified from recombinant baculoviral extracts), 0.25 μg hen egg lysozyme (HEL, Sigma, St. Louis, Mo.), 0.25 μg E. Coli β-galactosidase (β-gal, Sigma, St. Louis, Mo.), 2.2 μg mouse Id (Southern Biotech, Birmingham, Ala.), or 0.3 μg human Factor IX (Calbiochem, La Jolla, Calif.) in 50 μl BBS (89 mM Boric Acid, 90 mM NaCl pH 8.3) per well. Plates were incubated overnight at 4° C. then washed 4 times with BBST (BBS with 0.1% Tween 20). NP coated wells were blocked with 100 μl of NP assay buffer (5% nonfat milk in BBS) and wells of all other plates were blocked with 100 μl of BSA assay buffer (1% bovine serum albumin in BBS) for 1 hour at room temperature. Two-fold serial dilutions of sera in assay buffers, starting at 1:25, were prepared and 50 μl aliquots added to each well. Following a 2-hour incubation at room temperature and 4 washes, alkaline phosphatase conjugated goat anti-mouse IgG-Fc (Jackson Immunoresearch, West Grove, Pa.) diluted 1:5000 in assay buffer was added at 50 μl/well. The plates were incubated for 2 hours at room temperature, washed 4 times and 50 μl of p-NPP substrate (1 mg/ml paranitrophenyl phosphate, Calbiochem, La Jolla, Calif., in 50 mM sodium bicarbonate buffer, pH 9.8 and 1 mM $MgCl_2$) was added per well. The absorbance at 405 nm was read after 1.5 hours at room temperature. The titer is the reciprocal of the last dilution with a signal 2 times that of pre-bleed samples.

Antigen Specific IgG1 and IgG2a ELISAs

Alkaline phosphatase conjugated, mouse sub-isotype specific monoclonal antibodies were pre-titrated with standards to determine the dilution at which equal absorbance values were obtained for equal amounts of standard. For the titrations, plates were coated overnight at 4° C. with 0.1 μg/50 μl/well of affinity purified goat anti-mouse kappa antisera in BBS. Plates were washed and blocked as for the NP ELISA described above. Purified mouse IgG1, κ or IgG2a, κ were serially diluted and added to the plates at 50 μl/well. After incubating for 2 hours at room temperature, alkaline phosphatase conjugated rat anti-mouse IgG1 and IgG2a (Pharmingen, La Jolla, Calif.) were serially diluted and added to washed plates. The assay was completed as for the NP antibody ELISA. The assay for measurement of antigen specific sub-isotype serum titers was as described for total IgG levels with the following modifications: the alkaline phosphatase conjugated anti-mouse IgG1 and anti-mouse IgG2a were diluted 1:1500 and 1:200 respectively.

Stimulation of CTL

Spleens were removed from euthanized mice at 11-12 weeks after the first injection, and $2.5 \times 10^7$ splenocytes were cultured for 5 days in 6 well plates in a total of 5 ml of RPMI 1640 medium (unless otherwise noted, all tissue culture reagents were obtained from Gibco BRL Life Technologies, Rockville, Md.) containing L-glutamine and 25 mM HEPES and supplemented with penicillin (100 U/ml), streptomycin (100 μg/ml), $5.5 \times 10^{-5}$ M β-mercaptoethanol and 10% FBS (10% media) with either $NP_{147-155}$ peptide ($H-2K^d$ TYQR-TRALV) (SEQ ID NO: 1) or β-$gal_{876-884}$ peptide ($H-2L^d$ TPHPARIGL) (SEQ ID NO: 2) at 1 μg/ml and recombinant murine IL-2 (Roche Molecular Biochemicals, Indianapolis, Ind.) at 0.5 U/ml.

$^{51}$Cr Release Assay

To detect antigen specific lysis, P815 cells were labeled with 0.15 mCi $Na_2^{51}CrO_4$ (NEN Life Science Products, Boston, Mass.) and either pulsed with 20 μg $NP_{147-155}$ peptide or 50 μg β-$gal_{876-884}$ peptide in 1 ml RPMI 1640 media or were used unpulsed. Duplicate aliquots of stimulated splenocytes were serially diluted in 96 well round bottom plates (ICN Biomedicals, Aurora, Ohio) and target cells were added at the designated effector:target ratios in a final volume of 200 μl/well. The plates were centrifuged and incubated for 4 hours at 37° C. with 5% $CO_2$. After incubation, 100 μl of supernatant from each well was analyzed. Specific lysis was calculated as % specific lysis=$[(a-b)/(c-b)]100$ where a is the average cpm released in the presence of effectors, b is the average cpm released from target cells incubated in media only and c is the cpm released from target cells in the presence of 1% Triton-X 100.

Cytokine Profiles

To determine cytokine secretion profiles of spleen cells re-stimulated in vitro with antigen, splenocytes were plated in duplicate at $4 \times 10^5$ cells/100 μl/well in 96 well flat bottom culture plates with purified NP (purified from recombinant baculoviral extracts) or β-gal protein (Sigma, St. Louis, Mo.) at 5 μg/ml. Culture supernatants were harvested after 72 hours at 37° C. with 5% $CO_2$. Cytokines in culture supernatants were quantified with a mouse IFN-γ ELISA kit (Pharmingen, La Jolla, Calif.) and mouse IL-4 ELISA mini-kit (Endogen, Woburn, Mass.) according to the manufacturers' instructions.

Statistical Analysis

Statistical analyses were performed with the 2-tailed student t-test.

Effect of Vaxfectin on Antigen Specific IgG Titers

Antigen specific antibody titers for sera collected 1 day prior to the boost at 3 weeks, and for sera collected at 6 weeks following the first injection are shown in FIG. 11. Immunization with pDNA/Vaxfectin had a modest effect on the three-week titers of the anti-NP and anti-Factor IX antibodies and an even greater effect on the anti-mouse id and anti-HEL antibody titers. Vaxfectin had no effect on the serum titers of anti-β-gal antibodies at 3 weeks. Three weeks following the boost immunizations, titers for mice receiving pDNA/Vaxfectin were increased over those receiving naked pDNA for all five of the antigens. Table 3 summarizes the antigen specific IgG responses at 6 weeks for all 5 model antigens. Vaxfectin increased the titers of pDNA induced anti-NP and anti-HEL antibodies 8 fold and 10 fold respectively over naked pDNA and increased the titers of anti-β-gal, anti-factor IX and anti-mouse Id 3 fold over naked pDNA.

TABLE 3

| | IgG Antibody titers at 6 Weeks* | | |
|---|---|---|---|
| Antigen | Ab Titer for Naked (average ± std error) | Ab Titer for Vaxfectin (average ± std error) | Fold Increase with Vaxfectin |
| Influenza NP | 9,821 ± 1,418 | 74,933 ± 8,597 | 8 x |
| HEL | 14,300 ± 3,798 | 136,720 ± 27,096 | 10 x |
| β-gal | 27,280 ± 4,017 | 69,760 ± 12,544 | 3 x |

TABLE 3-continued

IgG Antibody titers at 6 Weeks*

| Antigen | Ab Titer for Naked (average ± std error) | Ab Titer for Vaxfectin (average ± std error) | Fold Increase with Vaxfectin |
|---|---|---|---|
| Mouse Id/Human Fc | 972 ± 381 | 2,503 ± 517 | 3 x |
| Human Factor IX | 10,240 ± 2,504 | 30,320 ± 6,752 | 3 x |

*Mice received a bilateral injection of 5 μg pDNA +/− Vaxfectin into each rectus femoris muscle at 0 and 3 weeks. Antibody titers were determined at 6 weeks (n = 20 for all groups, except for NP where n = 29 for Naked NP pDNA, n = 30 for NP p DNA/Vaxfectin, and for Mousde Idiotype where n = 19 for Naked Mouse Id p DNA).

Effect of Vaxfectin on the CTL Response

Plasmid DNA vaccination by the intramuscular route typically results in strong CTL responses to the encoded antigen (Ulmer et al., 1993; Raz et al., 1996; Donnelly et al., 1997). One possible outcome of formulating pDNA with an adjuvant to boost antibody responses is induction of a Th2 type response which could result in a weaker cell mediated immune response. To determine the effect of Vaxfectin on the pDNA induced CTL response, spleens from mice immunized with NP or β-gal pDNA were harvested 8-9 weeks following the boost injection. Splenocytes cultured with NP or n-gal peptide for 5-6 days were assayed for CTL lysis of P815 target cells pulsed with NP or β-gal peptide. Unpulsed P815 cells were used to detect non-specific lysis. The antigen specific CTL effector titration curves for % lysis of peptide pulsed target cells are shown in FIG. 12. The results for both NP and β-gal pDNA indicate that formulation of pDNA with Vaxfectin has no significant effect on the CTL response at any of the effector:target ratios tested (p>0.05 at all E:T ratios).

Effect of Vaxfectin on IgG1 and IgG2a Antibody Titers

The Th1 type immune responses induced by intramuscular pDNA immunization promote antibody heavy chain switch in responding B cells to the IgG2a sub-isotype (Raz et al., 1996). Thus production of antigen specific IgG2a is greater than antigen specific IgG1. The use of an adjuvant in pDNA vaccines could qualitatively change the immune response, resulting in greater production of either IgG1 or IgG2a. To determine the effect of Vaxfectin on the relative proportion of antigen specific serum IgG1 to IgG2a when formulated with various antigen plasmid DNAs, 6 week sera were analyzed for antigen specific sub-isotype titers.

Figure 13A:
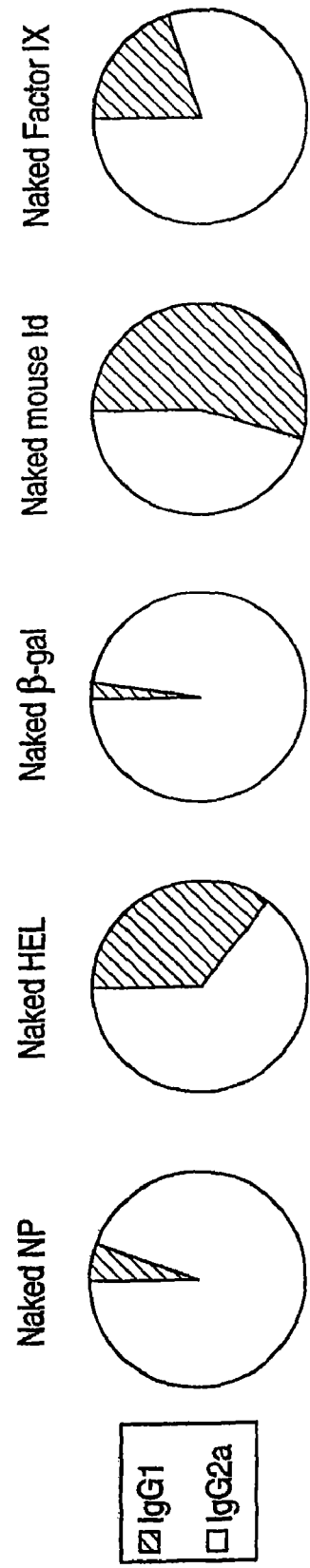
FIGS. 13A and 13B illustrate the Th1 type isotype profiles of antigen specific antibodies induced with 5 different pDNA encoded model antigens. Serum titers of antigen specific sub-isotypes are presented as a percentage of the sum of IgG1 and IgG2a titers. (n=20 for all groups, except for NP where n=29 for Naked NP pDNA; n=30 for NP pDNA/Vaxfectin and mouse Id where n=19 for naked pDNA.) A) Percent of IgG1 and IgG2a at 6 weeks following naked pDNA immunizations. B) Percent of IgG1 and IgG2a at 6 weeks following pDNA/Vaxfectin immunizations.
Figure 13B:
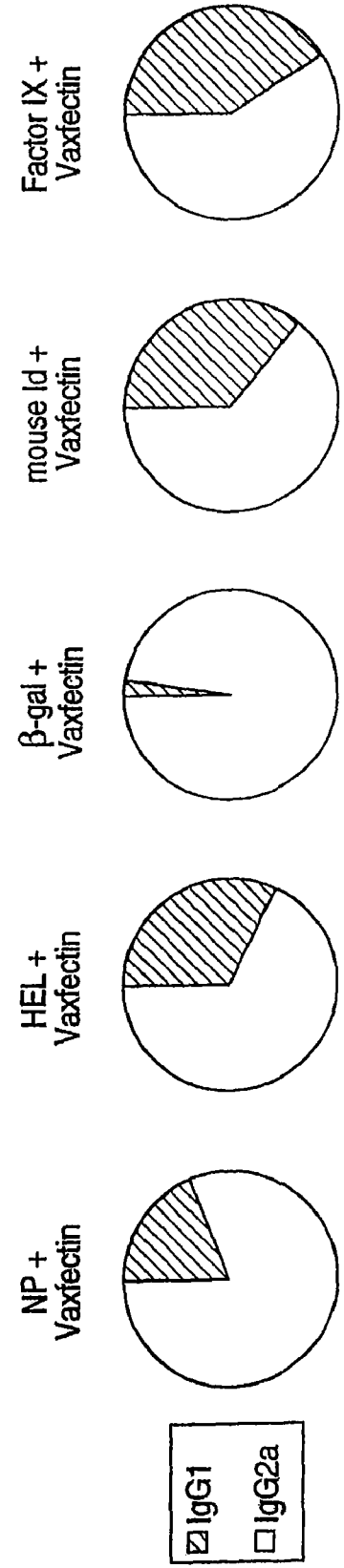

As shown in FIG. 13a, immunizations with naked pDNA encoding different antigens result in sub-isotype profiles that are unique to each antigen. Although the relative proportion of IgG1 and IgG2a varied for different antigens, IgG2a was the predominant sub-isotype produced, consistent with a Th1 type immune response. Vaxfectin formulated with all five model antigen pDNAs results in an increase of both antigen specific antibody sub-isotypes (Table 4). Increases in antigen specific IgG1 and IgG2a were approximately the same magnitude for Vaxfectin formulated pDNA for 4 of the model antigens. As compared to titers obtained with naked pDNA, formulating pDNA with Vaxfectin increased anti-HEL IgG1 titers 9-fold and IgG2a titers 11-fold. Vaxfectin increased anti-β-gal, anti-mouse Id/human Fc and anti-factor IX IgG1 titers 2 to 5-fold and IgG2a titers 2 to 4-fold over naked DNA. Vaxfectin formulated with NP pDNA increased the average anti-NP IgG1 antibody titer by 15-fold over naked pDNA. However, the average anti-NP IgG2a antibody titer was only increased 3-fold. Thus, the relative proportions of IgG1 and IgG2a elicited by immunization of pDNA/Vaxfectin remains similar to the proportions generated when naked pDNA is used to immunize mice except in the case of NP pDNA/Vaxfectin (FIG. 13b). In this case, there is a much greater increase in antibody titer of anti-NP IgG1 than anti-NP IgG2a. For all of the pDNAs formulated with Vaxfectin, titers of antigen specific IgG2a were higher than antigen specific IgG1, suggesting a Th1 type response.

TABLE 4

IgG1 and IgG2a antibody titers at 6 weeks*

| Isotype | Influenza NP | | HEL | | β-gal | | Mouse Id/Human Fc | | Human Factor IX | |
|---|---|---|---|---|---|---|---|---|---|---|
|  | IgG1 | IgG2a | IgG1 | IgG2a | IgG1 | IgG2a | IgG1 | IgG2a | IgG1 | IgG2a |
| Naked PDNA | 11,172 ± 1,825 | 213,628 ± 60,785 | 14,210 ± 3,364 | 25,620 ± 6,719 | 8,620 ± 1,887 | 356,480 ± 67,452 | 493 ± 339 | 426 ± 228 | 6,700 ± 1,789 | 25,680 ± 9,999 |
| PDNA/Vaxfectin | 171,467 ± 44,030 | 745,813 ± 161,747 | 128,340 ± 28,009 | 280,720 ± 61,683 | 16,100 ± 6,807 | 944,640 ± 337,513 | 878 ± 281 | 1,615 ± 638 | 35,380 ± 9,449 | 53,280 ± 11,449 |
| Increase over Naked | 15 X | 3 X | 9 X | 11 X | 2 X | 3 X | 2 X | 4 X | 5 X | 2 X |

*Mice received a bilateral injection of 5 μg pDNA +/− Vaxfectin into each rectus femoris muscle at 0 and 3 weeks. Antibody titers were determined at 6 weeks (n = 20 for all groups, except for NP where n = 29 for Naked NP pDNA, n = 30 for NP pDNA/Vaxfectin, and for Mouse Idiotype where n = 19 for Naked Mouse Id pDNA).

Effect of Vaxfectin on the Cytokine Profile

The antigen specific antibody sub-isotype analyses suggest that the responses induced with Vaxfectin formulated pDNA, as for naked pDNA are Th1 type responses. To confirm that Vaxfectin has no effect on the Th cytokine profile in an antigen specific in vitro recall response, spleens from groups of mice immunized with NP or β-gal pDNA formulated with or without Vaxfectin were harvested 8-9 weeks following the boost injection. Splenocytes were cultured and stimulated with NP or n-gal protein. Supernatants harvested from the cultured cells were assayed for IFN-γ and IL-4 production. Immunizations with NP or β-gal plasmid DNA formulated with or without Vaxfectin resulted in IFN-γ production in splenocyte cultures from all groups of immunized mice (FIG. 14). Low levels of IL-4 were produced in all groups of mice; however, IFN-γ was the predominant cytokine produced, suggesting a Th1 biased response.

In summary, the foregoing examples demonstrate the robust adjuvant effects of a unique cationic lipid-based formulation for nucleic acid vaccines. The stimulation of the humoral response can be accomplished without diminishing the strong cytolytic responses typical of nucleic acid-based vaccines. The adjuvant activity is seen in both mice and rabbits, thus implying the pharmaceutical applications in other mammals, as well as offering potential benefit in nucleic acid-based preparation of monoclonal and polyclonal antibodies. GAP-DMORIE/co-lipid (e.g., Vaxfectin) mediated enhancement of the antibody responses was readily observed after a single unilateral intramuscular injection. This is important for the immunization of farm animals where single-shot vaccines are highly desirable since roundup of range animals is expensive and can result in loss of production due to stress (Beard, C. W., et al, *Nat. Biotechnol* 16(13), 1325-1328 (1998)).

Example 5

Human Administration

Immunogenic compositions comprising pDNA encoding hemagglutinin (HA), mixed with an adjuvant containing GAP-DMORIE formulated as a 1:1 (mol:mol) mixture with DPyPE, are prepared according to the method described above. The pDNA/adjuvant molar ratio is 4:1. Three injections of 0.1, 0.5, 1.0, or 2.5 mg pDNA in physiological saline, as a complex with the adjuvant, are injected into humans at 4-week intervals in alternate deltoids. Serum is removed from the humans and the HA antibody levels are determined by serial dilution using a standard ELISA assay, as described above. Immune responses of the human subjects to the HA antibody are induced, as indicated by GMT antibody titer values.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing the immune response to a parasitic infection in a mammal comprising administering to the mammal an immunogenic composition comprising:

(a) one or more immunogen-encoding polynucleotides, immunogenic polypeptides, or polysaccharides from the parasitic infection, in an amount sufficient to increase the immune response in the mammal to the polynucleotides, polypeptides, or polysaccharides; and (b) an adjuvant comprising a (±)-N-(3-aminopropyl)-N,N-dimethyl-2,3-bis(syn-9-tetradeceneyloxy)-1-propanaminium salt and one or more co-lipids, wherein the immune response to the parasitic infection is increased in the mammal.

2. The method of claim 1 wherein the (±)-N-(3-aminopropyl)-N,N-dimethyl-2,3-bis(syn-9-tetradeceneyloxy)-1-propanaminium salt is (±)-N-(3-aminopropyl)-N,N-dimethyl-2,3-bis(syn-9-tetradeceneyloxy)-1-propanaminium bromide (GAP-DMORIE).

3. The method of claim 1 wherein the co-lipid is a phosphatidylethanolamine.

4. The method of claim 3 wherein the phosphatidylethanolamine is 1,2-dioleoyl-sn-glycero-3-phosphoethanolamine (DOPE).

5. The method of claim 3 wherein the phosphatidylethanolamine is 1,2-diphytanoyl-sn-glycero-3-phosphoethanolamine (DPyPE).

6. The method of claim 1 wherein the (±)-N-(3-aminopropyl)-N,N-dimethyl-2,3-bis(syn-9-tetradeceneyloxy)-1-propanaminium salt and the co-lipid are in a molar ratio of from about 9:1 to about 1:9.

7. The method of claim 3, wherein the phosphatidylethanolamine is 1,2-dimyristoyl-glycer-3-phosphoethanolamine (DMPE).

8. The method of claim 1, wherein the molar ratio of (±)-N-(3-aminopropyl)-N,N-dimethyl-2,3-bis(syn-9-tetradeceneyloxy)-1-propanaminium salt to co-lipid is from about 4:1 to about 1:4.

9. The method of claim 1, wherein the molar ratio of (±)-N-(3-aminopropyl)-N,N-dimethyl-2,3-bis(syn-9-tetradeceneyloxy)-1-propanaminium salt to co-lipid is from about 2:1 to about 1:2.

10. The method of claim 1, wherein the molar ratio of (±)-N-(3-aminopropyl)-N,N-dimethyl-2,3-bis(syn-9-tetradeceneyloxy)-1-propanaminium salt to co-lipid is about 1:1.

11. The method of claim 1, wherein the mammal is a human.

12. The method of claim 1, wherein the immunogenic composition further comprises an excipient.

13. The method of claim 1, wherein the administration is intravenous.

14. The method of claim 1, wherein the administration is by a route selected from the group consisting of intramuscular, intratracheal, intranasal, transdermal, interdermal, subcutaneous, intraocular, vaginal, rectal, intraperitoneal, intraintestinal, and inhalation.

15. The method of claim 1, wherein the polynucleotide is DNA, RNA or a nucleic acid oligomer from the parasitic infection.

16. The method of claim 1 wherein the polynucleotide is a linear or circular polynucleotide from the parasitic infection.

17. The method of claim 1 wherein the polynucleotide is all or part of a plasmid DNA from the parasitic infection.

* * * * *